United States Patent
Hardy et al.

(10) Patent No.: US 6,300,540 B1
(45) Date of Patent: *Oct. 9, 2001

(54) TRANSGENIC MOUSE EXPRESSING AN APP-FAD DNA SEQUENCE

(75) Inventors: John Anthony Hardy, Tampa, FL (US); Marie-Christine Chartier-Harlin, Villeneuve d'Ascq (FR); Alison Mary Goate, St. Louis, MO (US); Michael John Owen, South Glamorgan (GB); Michael John Mullan, Tampa, FL (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 08/464,250

(22) Filed: Jun. 5, 1995

Related U.S. Application Data

(63) Continuation of application No. 08/104,165, filed as application No. PCT/GB92/00123 on Jan. 21, 1992, now Pat. No. 5,877,015.

(30) Foreign Application Priority Data

Jan. 21, 1991 (GB) .................................................. 9101307
Aug. 28, 1991 (GB) .................................................. 9118445

(51) Int. Cl.$^7$ ...................... A01K 67/027; A01K 67/033; G01N 33/00
(52) U.S. Cl. .................................. 800/18; 800/3; 800/12
(58) Field of Search ................................. 800/2, DIG. 1, 800/3, 12, 18; 536/23.1

(56) References Cited

U.S. PATENT DOCUMENTS

| | | |
|---|---|---|
| 4,666,829 | 5/1987 | Glenner et al. . |
| 5,134,062 | 7/1992 | Blass . |
| 5,200,339 | 4/1993 | Abraham . |
| 5,234,814 | 8/1993 | Card et al. . |
| 5,387,742 | 2/1995 | Cordell . |
| 5,612,486 | 3/1997 | McConlogue .......................... 800/2 |
| 5,877,015 | 3/1999 | Hardy et al. ........................ 435/325 |
| 5,879,883 | 3/1999 | Benson et al. ........................... 435/6 |

FOREIGN PATENT DOCUMENTS

| | | | |
|---|---|---|---|
| 123 527 | 10/1984 | (EP) | ............................. G01N/33/54 |
| 171 496 | 2/1986 | (EP) | ............................. C12N/15/00 |
| 173 494 | 3/1986 | (EP) | ............................. C12N/15/00 |
| 184 187 | 6/1986 | (EP) | ............................. C12N/15/00 |
| 276 723 | 12/1993 | (EP) . | |
| 62-100291 | 5/1987 | (JP) | ............................. C12N/15/00 |
| WO 86/01533 | 3/1986 | (WO) | ............................. C12N/15/00 |
| WO 87/02671 | 5/1987 | (WO) | ............................. C07H/15/12 |
| WO 91/16628 | 10/1991 | (WO) | ............................. G01N/33/53 |
| WO 91/19810 | 12/1991 | (WO) | ............................. C12P/21/00 |
| WO 92/00521 | 1/1992 | (WO) | ............................. G01N/33/00 |
| WO 92/09699 | 6/1992 | (WO) | ............................. C12P/21/08 |

OTHER PUBLICATIONS

Selkoe (1991) Nature 354, 432–433.*
Lannfelt et al (1993) Behav. Brain Res. 57, 207–213.*
Podlisny et al (1992) Neurobiol. Aging 13, 56–567.*
Games et al. (1992) Neurobiol. Aging 13, 569–576.*
Felsenstein et al (1995) Alz. Parkinson Diseases, Hanin, ed, Plenum Press, NY, pp. 401–409.*
Felsenstein et al (1994) Nature Genetics 6, 251–256.*
Yoshioka et al (1991) Biochem. Biophy. Res. Comm. 178, 1141–1146.*
Games et al (1995) Nature 373, 523–527.*
Hsio et al (1996) Science 274, 99–102.*
Abraham et al., "A calcium–activated protease from Alzheimer's disease brain cleaves at the N–terminus of the amyloid β–protein," (1991) *Biochem. Biophys. Res. Comm.* 174:790–796.
Chartier–Harlan et al., "Early–onset Alzheimer's disease caused by mutations at codon 717 of the β–amyloid precursor protein gene," (1991) *Nature* 353:844–846.
Esch et al., "Cleavage of amyloid β peptide during constitutive processing of its precursor," (1990) *Science* 248:1122–1124.
Estus et al., "Potentially amyloidogenic, carboxyl–terminal derivatives of the amyloid protein precursor," (1992) *Science* 255:726–728.
Forss–Petter et al., "Transgenic mice expressing β–galactosidase in mature neurons under neuron–specific enolase promoter control," (1990) *Neuron* 5:187–197.
Glenner et al., "Alzheimer's disease: initial report of the purification and characterization of a novel cerebrovascular amyloid protein," (1984) *Biochem. Biophys. Res. Commun.* 120:885–890.
Glenner et al., "Alzheimer's disease and Down's syndrome: sharing of unique cerebrovascular amyloid fibril protein," (1984) *Biochem. Biophys. Res. Commun.* 122:1131–1135.
Goate et al., "Segregation of a missense mutation in the amyloid precursor protein gene with familial Alzheimer's disease," (1991) Nature 349:704–706.
Goding, James W. "Production and application of monoclonal antibodies in cell biology, biochemistry and immunology," in *Monoclonal Antibodies: Principles and Practice*, Ch. 3, pp. 56–74 (Academic Press, London 1984).
Golde et al., "Processing of the amyloid protein precursor to potentially amyloidogenic derivatives," (1992) *Science* 255:728–730.

(List continued on next page.)

Primary Examiner—Deborah Crouch
(74) Attorney, Agent, or Firm—Townsend and Townsend and Crew LLP

(57) ABSTRACT

Model systems of Alzheimer's disease comprise a DNA sequence encoding an amyloid precursor protein (APP) isoform or fragment that has an amino acid substitution. The substituted amino acid may be other than valine at the amino acid position corresponding to amino acid residue position 717 of APP770. Methods of determining genetic predisposition to Alzheimer's disease are also disclosed.

6 Claims, 29 Drawing Sheets

OTHER PUBLICATIONS

Haass et al., "Amyloid β–peptide is produced by cultured cells during normal metabolism," (1992) *Nature* 359:322–325.

Hyman et al., "Kunitz protease inhibitor–containing amyloid β protein precursor immunoreactivity in Alzheimer's disease," (1992) *J. Neuropath. Exp. Neurol.* 51:76–83.

Kang et al., "The precursor of Alzheimer's disease amyloid A4 protein resembles a cell–surface receptor," (1987) *Nature* 325:733–736.

Kennedy et al., "Only Kunitz–inhibitor–containing isoforms of secreted Alzheimer amyloid precursor protein show amyloid immunoreactivity in normal cerebrospinal fluid," (1992) *Neurodegeneration* 1:59–64.

Kitaguchi et al., "Novel precursor of Alzheimer's disease amyloid protein shows protease inhibitory activity," (1988) *Nature* 331:530–532.

Mullan et al., "A pathogenic mutation for probable Alzheimer's disease in the APP gene at the N–terminus of β–amyloid," (1992) *Nature Genetics* 1:345–347.

Murrell et al., "A mutation in the amyloid precursor protein associated with hereditary Alzheimer's disease," (1991) *Science* 254:97–99.

Oltersdorf et al., "The Alzheimer's amyloid precursor protein: Identification of a stable intermediate in the biosynthetic/degradative pathway," (1990) *J. Biol. Chem.* 265:4492–4497.

Oltersdorf et al. "The secreted form of the Alzheimer's amyloid precursor protein with the Kunitz domain is protease nexin–II," (1989) *Nature* 341:144–147.

Palmert et al., "Soluble derivatives of the β amyloid protein precursor of Alzheimer's disease are labeled by antisera to the β amyloid protein," (1989) *Biochem. Biophys. Res. Comm.* 165:182–188.

Palmert et al., "The β–amyloid protein precursor of Alzheimer disease has soluble derivatives found in human brain and cerebrospinal fluid," (1989) *Proc. Natl. Acad. Sci USA* 86:6338–6342.

Ponte et al., "A new A4 amyloid mRNA contains a domain homologous to serine proteinase inhibitors," (1988) *Nature* 331:525–527.

Pulliam et al., "Use of aggregating brain cultures to study the replication of herpes simplex virus types 1 and 2 in central nervous system tissue," (1984) *J. Virol. Met.* 9:301–316.

Quon et al., "Formation of β–amyloid protein deposits in brains of transgenic mice," *Nature* 352, 239–241 (1991).

Selkoe et al., "β–amyloid precursor protein of Alzheimer disease occurs as 110– to 135–kilodalton membrane–associated proteins in neural and nonneural tissues," (1988) *Proc. Natl. Acad. Sci. USA* 85:7341–7345.

Seubert et al., "Isolation and quantification of soluble Alzheimer's β–peptide from biological fluids," (1992) *Nature* 359:325–327.

Weidemann et al., "Identification, biogenesis, and localization of precursors of Alzheimer's disease A4 amyloid protein," (1989) *Cell* 57:115–126.

Chartier–Harlin et al., *Neurosci. Lett.* 129:134 (1991).

de Sauvage et al., *Science* 245:651 (1989).

Golde et al., *Neuron* 4:253 (1990).

Hardy et al., *Lancet* 337:1342–1343 (1991).

Harrison et al., *Neurorep.* 2:152 (1991).

Hyslop et al., *Science* 235:885 (1987).

Johnstone et al., *Mol. Brain Res.* 10:299 (1991).

Kawabata et al., *Nature* 354:476 (1991).

Rumble et al., *New Eng. J. Med.* 320:1446 (1989).

Salbaum et al., *EMBO* 7(9):2807 (1988).

Schellenberg et al., *Science* 241:1507 (1988).

Schilling et al., *Gene* 98(2):225 (1991).

Sisodia, *Science* 248:492 (1990).

Tanzi et al., *Nature* 329:156 (1987).

Tanzi et al., *Nature* 350:564 (1991).

Van Broekhoven et al., *Nature* 329:153 (1987).

Wirak et al., *EMBO* 10:289 (1991).

Wirak et al., *Science* 253:323 (1991).

Yoshikai et al., *Gene* 87:257 (1990).

Selkoe, "Amyloid Protein and Alzheimer's Disease," *Scientific American*, 265(5):40–47 (1991).

Kazazian, Haig H., "Sequencing of the Alzheimer's APP Gene Dutch Variant (APP–D)," *Human Mutation*, 2:495 (1993).

Levy et al., "Mutation of the Alzheimer's Disease Amyloid Gene in Hereditary Cerebral Hemorrhage, Dutch Type," *Science*, 248:11241126 (1990).

Malow et al., "Cultured cells as a screen for novel treatments of Alzheimer's disease," *Arch. Neurol.*, 46(11):1201–1203 (1989).

Miller et al., "Alzheimer's disease: transgenic models to test new chemicals and pharmaceuticals," *Curr. Opin. Biotechnology*, 3:683–686 (1992).

Mowshowitz et al., "Antiviral response of fibroblasts from familial alzheimer's disease and Down's syndrome to human interferon–alpha," *J. Neural Transmission*, 57(1–2):121–126 (1983).

Scuderio et al., "Alzheimer's disease fibroblasts are hypersensitive to the lethal effects of a DNA–damaging chemical," *Mutation Research*, 159(1–2):125–131 (1986).

Westphal, H., "Mouse models of human diseases," *Curr. Opin. Biotech.*, 2:830–833 (1991).

Zemlan et al., "Superoxide dismutase activity in Alzheimer's disease: possible mechanism for paired helical filament formation," *Brain Res.*, 476(1):160–162 (1989).

* cited by examiner

FIG. 7 (1/7)

```
Met Leu Pro Gly Leu Ala Leu Leu Leu Ala Ala Trp Thr Ala Arg
 1               5                  10                  15
Ala Leu Glu Val Pro Thr Asp Gly Asn Ala Gly Leu Leu Ala Glu Pro
                20                  25                  30
Gln Ile Ala Met Phe Cys Gly Arg Leu Asn Met His Met Asn Val Gln
             35                  40                  45
Asn Gly Lys Trp Asp Ser Asp Pro Ser Gly Thr Lys Thr Cys Ile Asp
 50                  55                  60
Thr Lys Glu Gly Ile Leu Gln Tyr Cys Gln Glu Val Tyr Pro Glu Leu
 65                  70                  75                  80
Gln Ile Thr Asn Val Val Glu Ala Asn Gln Pro Val Thr Ile Gln Asn
                85                  90                  95
Trp Cys Lys Arg Gly Arg Lys Gln Cys Lys Thr His Pro His Phe Val
                    100                 105                 110
```

FIG.7 (2/7)

```
Ile Pro Tyr Arg Cys Leu Val Gly Glu Phe Val Ser Asp Ala Leu Leu
    115                 120                 125
Val Pro Asp Lys Cys Lys Phe Leu His Gln Glu Arg Met Asp Val Cys
    130                 135                 140
Glu Thr His Leu His Trp His Thr Val Ala Lys Glu Thr Cys Ser Glu
    145                 150                 155                 160
Lys Ser Thr Asn Leu His Asp Tyr Gly Met Leu Leu Pro Cys Gly Ile
                        165                 170                 175
Asp Lys Phe Arg Gly Val Glu Phe Val Cys Cys Pro Leu Ala Glu Glu
                180                 185                 190
Ser Asp Asn Val Asp Ser Ala Asp Ala Glu Glu Asp Asp Ser Asp Val
            195                 200                 205
```

FIG. 7 (3/7)

```
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu
225                 230                 235                 240
Glu Ala Asp Asp Asp Glu Asp Asp Glu Gly Asp Glu Val Glu Glu
                    245                 250                 255
Glu Ala Glu Glu Pro Tyr Glu Glu Ala Thr Glu Arg Thr Thr Ser Ile
            260                 265                 270
Ala Thr Thr Thr Thr Thr Thr Thr Glu Ser Val Glu Glu Val Val Arg
    275                 280                 285
Val Pro Thr Thr Ala Ala Ser Thr Pro Asp Ala Val Asp Lys Tyr Leu
290                 295                 300
```

FIG. 7 (4/7)

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
            325                 330                 335

Glu Trp Glu Glu Ala Glu Arg Gln Ala Lys Asn Leu Pro Lys Ala Asp
        340                 345                 350

Lys Lys Ala Val Ile Gln His Phe Gln Glu Lys Val Glu Ser Leu Glu
355                 360                 365

Gln Glu Ala Ala Ala Asn Glu Arg Gln Gln Leu Val Glu Thr His Met Ala
370                 375                 380

Arg Val Glu Ala Met Leu Asn Asp Arg Arg Arg Leu Ala Leu Glu Asn
385                 390                 395                 400

FIG. 7 (5/7)

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
                435                 440                 445

Ala Gln Ile Arg Ser Gln Val Met Thr His Leu Arg Val Ile Tyr Glu
                450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

FIG. 7(6/7)

Tyr Ser Asp Asp Val Leu Ala Asn Met Ile Ser Glu Pro Arg Ile Ser
500                                     505                     510

Tyr Gly Asn Asp Ala Leu Met Pro Ser Leu Thr Glu Thr Lys Thr Thr
         515                     520                     525

Val Glu Leu Leu Pro Val Asn Gly Glu Phe Ser Leu Asp Asp Leu Gln
530                     535                     540

Pro Trp His Ser Phe Gly Ala Asp Ser Val Pro Ala Asn Thr Glu Asn
545                     550                     555                 560

Glu Val Glu Pro Val Asp Ala Arg Pro Ala Ala Asp Arg Gly Leu Thr
         565                     570                     575

Thr Arg Pro Gly Ser Gly Leu Thr Asn Ile Lys Thr Glu Glu Ile Ser
         580                     585                     590

FIG. 7 (7/7)

```
Glu Val Lys Met Asp Ala Glu Phe Arg His Asp Ser Gly Tyr Glu Val
            595                 600                 605
His His Gln Lys Leu Val Phe Phe Ala Glu Asp Val Gly Ser Asn Lys
            610                 615                 620
Gly Ala Ile Ile Gly Leu Met Val Gly Gly Val Val Ile Ala Thr Val
            625                 630                 635                 640
Ile Val Ile Thr Leu Val Met Leu Lys Lys Lys Gln Tyr Thr Ser Ile
            645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
            675                 680                 685
Phe Phe Glu Gln Met Gln Asn
            690                 695
```

FIG. 8 (1/8)

```
Met Leu Pro Gly Leu Ala Leu Leu Leu Ala Ala Trp Thr Ala Arg
 1               5                  10                  15
Ala Leu Glu Val Pro Thr Asp Gly Asn Ala Gly Leu Leu Ala Glu Pro
                20                  25                  30
Gln Ile Ala Met Phe Cys Gly Arg Leu Asn Met His Met Asn Val Gln
                35                  40                  45
Asn Gly Lys Trp Asp Ser Asp Pro Ser Gly Thr Lys Thr Cys Ile Asp
    50                  55                  60
Thr Lys Glu Gly Ile Leu Gln Tyr Cys Gln Glu Val Tyr Pro Glu Leu
    65                  70                  75                  80
Gln Ile Thr Asn Val Val Glu Ala Asn Gln Pro Val Thr Ile Gln Asn
                85                  90                  95
Trp Cys Lys Arg Gly Arg Lys Gln Cys Lys Thr His Pro His Phe Val
                100                 105                 110
```

FIG. 8(2/8)

```
Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
            145                 150                 155             160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205
```

FIG.8(3/8)

```
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                    245                 250                 255
Glu Ala Glu Glu Pro Tyr Glu Glu Ala Thr Arg Thr Arg Thr Ser Ile
                    260                 265                 270
Ala Thr Thr Thr Thr Thr Thr Thr Glu Ser Val Glu Glu Val Val Arg
            275                 280                 285
Glu Val Cys Ser Glu Gln Ala Glu Thr Gly Pro Cys Arg Ala Met Ile
290                 295                 300
```

FIG. 8 (4/8)

```
Ser Arg Trp Tyr Phe Asp Val Thr Glu Gly Lys Cys Ala Pro Phe Phe
305                 310                 315                 320
Tyr Gly Gly Cys Gly Gly Asn Arg Asn Asn Phe Asp Thr Glu Glu Tyr
        325                 330                 335
Cys Met Ala Val Cys Gly Ser Ala Ile Pro Thr Thr Ala Ala Ser Thr
                340                 345                 350
Pro Asp Ala Val Asp Lys Tyr Leu Glu Thr Pro Gly Asp Glu Asn Glu
        355                 360                 365
His Ala His Phe Gln Lys Ala Lys Glu Arg Leu Glu Ala Lys His Arg
                370                 375                 380
Glu Arg Met Ser Gln Val Met Arg Glu Trp Glu Glu Ala Glu Arg Gln
385                 390                 395                 400
```

FIG. 8 (5/8)

```
Ala Lys Asn Leu Pro Lys Ala Asp Lys Lys Ala Val Ile Gln His Phe
                405                 410                 415
Gln Glu Lys Val Glu Ser Leu Glu Gln Glu Ala Ala Asn Glu Arg Gln
            420                 425                 430
Gln Leu Val Glu Thr His Met Ala Arg Val Glu Ala Met Leu Asn Asp
        435                 440                 445
Arg Arg Arg Leu Ala Leu Glu Asn Tyr Ile Thr Ala Leu Gln Ala Val
    450                 455                 460
Pro Pro Arg Pro Arg His Val Phe Asn Met Leu Lys Lys Tyr Val Arg
465                 470                 475                 480
Ala Glu Gln Lys Asp Arg Gln His Thr Leu Lys His Phe Glu His Val
                485                 490                 495
```

FIG. 8 (6/8)

```
Arg Met Val Asp Pro Lys Lys Ala Ala Gln Ile Arg Ser Gln Val Met
              500                 505                 510

Thr His Leu Arg Val Ile Tyr Glu Arg Met Asn Gln Ser Leu Ser Leu
              515                 520                 525

Leu Tyr Asn Val Pro Ala Val Ala Glu Ile Gln Asp Glu Val Asp
              530                 535                 540

Glu Leu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
                    565                 570                 575

Ser Leu Thr Glu Thr Lys Thr Thr Val Glu Leu Leu Pro Val Asn Gly
580                 585                 590
```

FIG. 8 (7/8)

Ser Leu Thr Glu Thr Lys Thr Thr Val Glu Leu Leu Pro Val Asn Gly
               580                 585                 590

Glu Phe Ser Leu Asp Asp Leu Gln Pro Trp His Ser Phe Gly Ala Asp
               595                 600                 605

Ser Val Pro Ala Asn Thr Glu Asn Glu Val Glu Pro Val Asp Ala Arg
               610                 615                 620

Pro Ala Ala Asp Arg Gly Leu Thr Thr Arg Pro Gly Ser Gly Leu Thr
               625                 630                 635                 640

Asn Ile Lys Thr Glu Glu Ile Ser Glu Val Lys Met Asp Ala Glu Phe
               645                 650                 655

FIG. 8 (8/8)

Arg His Asp Ser Gly Tyr Glu Val His His Gln Lys Leu Val Phe Phe
                660                 665                 670

Ala Glu Asp Val Gly Ser Asn Lys Gly Ala Ile Ile Gly Leu Met Val
                675                 680                 685

Gly Gly Val Val Ile Ala Thr Val Ile Val Ile Thr Leu Val Met Leu
                690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn
                740                 745                 750

FIG. 9 (1/8)

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His His Pro His Phe Val
                100                 105                 110
```

FIG. 9 (2/8)

```
Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
            130                 135                 140

Glu Thr His Leu His Trp His Thr Val Ala Lys Glu Thr Cys Ser Glu
            145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205
```

FIG.9(3/8)

```
Trp Trp Gly Gly Ala Asp Thr Asp Tyr Ala Asp Gly Ser Glu Asp Lys
210                 215                 220
Val Val Glu Val Ala Glu Glu Glu Val Ala Glu Val Glu Glu Glu
225                 230                 235                 240
Glu Ala Asp Asp Asp Glu Asp Asp Glu Asp Gly Asp Glu Val Glu Glu
                    245                 250                 255
Glu Ala Glu Glu Pro Tyr Glu Glu Ala Thr Glu Arg Thr Thr Ser Ile
            260                 265                 270
Ala Thr Thr Thr Thr Thr Thr Thr Glu Ser Val Glu Glu Val Val Arg
275                 280                 285
Glu Val Cys Ser Glu Gln Ala Glu Thr Gly Pro Cys Arg Ala Met Ile
290                 295                 300
```

FIG. 9 (4/8)

```
Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Met Ser Gln Ser Leu Leu Lys Thr
                340                 345                 350

Thr Gln Glu Pro Leu Ala Arg Asp Pro Val Lys Leu Pro Thr Thr Ala
                355                 360                 365

Ala Ser Thr Pro Asp Ala Val Asp Lys Tyr Leu Glu Thr Pro Gly Asp
        370                 375                 380

Glu Asn Glu His Ala His Phe Gln Lys Ala Lys Glu Arg Leu Glu Ala
385                 390                 395                 400
```

FIG.9(5/8)

Lys His Arg Glu Arg Met Ser Gln Val Met Arg Glu Trp Glu Glu Ala
            405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
            435                 440                 445

Glu Arg Gln Gln Leu Val Glu Thr His Met Ala Arg Val Glu Ala Met
            450                 455                 460

Leu Asn Asp Arg Arg Arg Leu Ala Leu Glu Asn Tyr Ile Thr Ala Leu
            465                 470                 475                 480

Gln Ala Val Pro Pro Arg Pro Arg His Val Phe Asn Met Leu Lys Lys
            485                 490                 495

FIG. 9 (6/8)

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
            515                 520                 525

Gln Val Met Thr His Leu Arg Val Ile Tyr Glu Arg Met Asn Gln Ser
            530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
            565                 570                 575

Leu Ala Asn Met Ile Ser Glu Pro Arg Ile Ser Tyr Gly Asn Asp Ala
            580                 585                 590

FIG. 9 (7/8)

Leu Met Pro Ser Leu Thr Glu Thr Lys Thr Val Glu Leu Leu Pro
595                          600                          605

Val Asn Gly Glu Phe Ser Leu Asp Asp Leu Gln Pro Trp His Ser Phe
610                          615                          620

Gly Ala Asp Ser Val Pro Ala Asn Thr Glu Asn Glu Val Glu Pro Val
625                          630                          635                          640

Asp Ala Arg Pro Ala Ala Asp Arg Gly Leu Thr Thr Arg Pro Gly Ser
                             645                          650                          655

Gly Leu Thr Asn Ile Lys Thr Glu Glu Ile Ser Glu Val Lys Met Asp
                             660                          665                          670

Ala Glu Phe Arg His Asp Ser Gly Tyr Glu Val His His Gln Lys Leu
                             675                          680                          685

Val Phe Phe Ala Glu Asp Val Gly Ser Asn Lys Gly Ala Ile Ile Gly
690                          695                          700

FIG. 9 (8/8)

```
Val Phe Phe Ala Glu Asp Val Gly Ser Asn Lys Gly Ala Ile Ile Gly
690                 695                 700
Leu Met Val Gly Gly Val Val Ile Ala Thr Val Ile Val Ile Thr Leu
705                 710                 715                 720
Val Met Leu Lys Lys Gln Tyr Thr Ser Ile His His Gly Val Val
                725                 730                 735
Glu Val Asp Ala Ala Val Thr Pro Glu Arg His Leu Ser Lys Met
                740                 745                 750
Gln Gln Asn Gly Tyr Glu Asn Pro Thr Tyr Lys Phe Phe Glu Gln Met
                755                 760                 765
Gln Asn
770
```

TRANSGENIC MOUSE EXPRESSING AN APP-FAD DNA SEQUENCE

This is a continuation of application Ser. No. 08/104,165, now U.S. Pat. No. 5,877,015, the US National Phase of PCT/GB92/00123 filed Jan. 21, 1992.

BACKGROUND OF THE INVENTION

Alzheimer's disease is a progressive disease known generally as senile dementia. Broadly speaking the disease falls into two categories, namely late onset and early onset. Late onset, which occurs in old age (65+years), may be caused by the natural atrophy of the brain occurring at a faster rate and to a more severe degree than normal. Early onset Alzheimer's disease is much more infrequent but shows a pathologically identical dementia with diffuse brain atrophy which develops well before the senile period, i.e., between the ages of 35 and 60 years. There is evidence that one form of this type of Alzheimer's disease shows a tendency to run in families and is therefore known as familial Alzheimer's disease (FAD).

In both types of Alzheimer's disease the pathology is the same but the abnormalities tend to be more severe and more widespread in cases beginning at an earlier age. The disease is characterized by two types of lesions in the brain, these are senile plaques and neurofibrillary tangles.

Senile plaques are areas of disorganized neuropil up to 150 μm across with extracellular amyloid deposits at the center. Neurofibrillary tangles are intracellular deposits of amyloid protein consisting of two filaments twisted about each other in pairs.

The major protein subunit, β-amyloid protein, of the amyloid filaments of the senile plaque is a highly aggregating small polypeptide of approximate relative molecular mass 4,500. This protein is a cleavage product of a much larger precursor protein called amyloid precursor protein (APP).

At present there is no known effective therapy for the various forms of Alzheimer's disease (AD). However, there are several other forms of dementia for which treatment is available and which give rise to progressive intellectual deterioration closely resembling the dementia associated with Alzheimer's disease. A diagnostic test for AD would therefore provide a valuable tool in the diagnosis and treatment of these other conditions, by way of being able to exclude Alzheimer's disease. It will also be of value when a suitable therapy does become available.

Also important is the development of experimental models of Alzheimer's disease that can be used to define further the underlying biochemical events involved in AD pathogenesis. Such models could presumably be employed, in one application, to screen for agents that alter the degenerative course of Alzheimer's disease. For example, a model system of Alzheimer's disease could be used to screen for environmental factors that induce or accelerate the pathogenesis of AD. In contradistinction, an experimental model could be used to screen for agents that inhibit, prevent, or reverse the progression of AD. Presumably, such models could be employed to develop pharmaceuticals that are effective in preventing, arresting, or reversing AD.

SUMMARY OF THE INVENTION

The present invention provides model systems of Alzheimer's disease, wherein the model system comprises a DNA sequence encoding an arnyloid precursor protein (APP) isoform or fragment that has an amino acid other than valine at the amino acid position corresponding to amino acid residue position 717 of APP770.

In a first embodiment, the present invention provides an isolated DNA sequence that encodes an amyloid precursor protein (APP) isoform or fragment that has an amino acid other than valine at the amino acid position corresponding to amino acid residue position 717 of APP770.

In a second embodiment, the present invention provides a transgenic nonhuman animal that harbors at least one integrated copy of a human DNA sequence that encodes an amyloid precursor protein (APP) isoform or fragment that has an amino acid other than valine at the amino acid position corresponding to amino acid residue position 717 of APP770.

In a third embodiment, the present invention provides a transgenic nonhuman animal wherein at least one of the endogenous nonhuman APP alleles has been completely or partially replaced by all or a portion of a human APP gene that includes a codon 717 that does not encode valine.

In a fourth embodiment, the present invention provides cells, typically mammalian cells and preferably mammalian cells of the neural, glial, or astrocytic lineage, that have been transformed or transfected with a heterologous DNA sequence, or have been derived from a transgenic nonhuman animal, wherein the cells express an amyloid precursor protein (APP) isoform or fragment that has an amino acid other than valine at the amino acid position corresponding to amino acid residue position 717 of APP770. In accordance with standard protocols, cultured human cells, either primary cultures or immortalized cell lines, may be transfected, either transiently or stably, with a mutant APP allele so that the cultured human cell expresses a mutant APP polypeptide.

In a fifth embodiment, the present invention provides a method of producing transgenic nonhuman animals and transformed cells that contain a DNA sequence encoding an amyloid precursor protein (APP) isoform or fragment that has an amino acid other than valine at the amino acid position corresponding to amino acid residue position 717 of APP770.

In a sixth embodiment, the present invention provides a method of producing, free from other human proteins, a human amyloid precursor protein (APP) isoform or fragment that has an amino acid other than valine at the amino acid position corresponding to amino acid residue position 717 of APP770.

In a seventh embodiment, the present invention provides a human amyloid precursor protein (APP) isoform or fragment, free from other human proteins, that has an amino acid other than valine at the amino acid position corresponding to amino acid residue position 717 of APP770.

In an eighth embodiment, the invention provides a method for detecting an APP allele that is linked (i.e., cosegregates with) a genetic predisposition to Alzheimer's disease, particularly early onset AD, wherein such a pathognomonic APP allele is detected by determining that codon 717 of the allele does not encode valine, Preferably, a pathognomonic APP allele is detected when codon 717 is determined to encode either isoleucine, glycine, or phenylalanine. Thus, methods for locating the presence of genetic alterations associated with Alzheimer's disease are provided. This diagnostic method may be used to predict the development of the disease prior to onset, for genetic screening, or to detect a specific mutation in an experimental nonhuman animal or a cell.

In a ninth embodiment, the invention provides a human variant APP polypeptide free of other human proteins, typically present in a cell of a nonhuman animal. The invention also relates to an isolated nucleic acid encoding such a polypeptide and to uses and applications of such nucleic acid as are described above in relation to the specific embodiment of the invention which involves an amino acid substitution at position 717 (as defined in relation to APP770).

According to one aspect of the invention there is provided a method for detecting the presence, in a nucleic acid or other sample removed from a subject, of the gene for Alzheimer's disease comprising identifying a genetic alteration in a gene sequence coding for APP. Such genetic alterations may include mutations, insertions or deletions.

BRIEF DESCRIPTION OF THE FIGURES

FIG. 7 shows the sequence of APP695.

FIG. 8 shows the sequence of APP751.

FIG. 9 shows the sequence of APP770.

DETAILED DESCRIPTION OF THE PREFERRED EMBODIMENT

Figure 1:
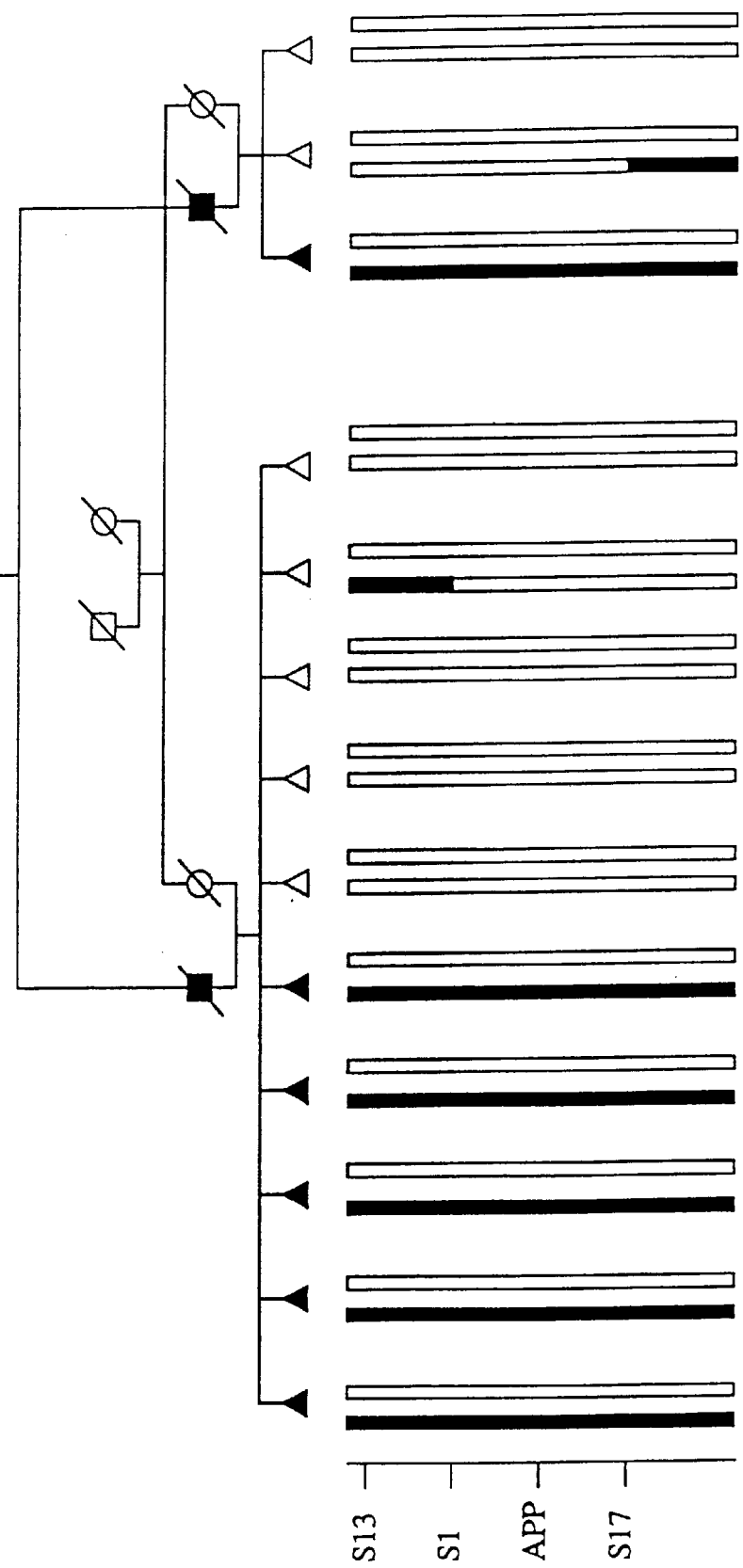
FIG. 1 illustrates a first pedigree in which early onset AD is apparently inherited as an autosomal dominant disorder. The average age of onset in this family is 57±5 years. Black symbols denote affected individuals and oblique lines indicate individuals who are deceased. Females are denoted by circles and males by squares. Triangles are used in the present generation to preserve anonymity. In generation II the spouses of the two affected brothers were sisters. Samples were available from the 13 individuals whose haplotypes are illustrated, from a further 19 children and spouses of these individuals and from 7 more distantly related unaffected individuals. Beneath the pedigree are ideograms of the two chromosomes 21 in each individual of the third generation at four loci on the long arm of the chromosome. The linkage data suggest that the black chromosomes were inherited from the affected fathers.

The accumulation of β-amyloid protein (A4) in particular brain regions is one of the main pathologic characteristics of Alzheimer's disease. The β-amyloid protein is an approximately 4 kD protein (39 to 42 amino acids) which is derived, as an internal cleavage product, from one or more isoforms of a larger amyloid precursor protein (APP). There are at least five distinct isoforms of APP containing 563, 695, 714, 751, and 770 amino acids, respectively (Wirak et al. (1991) *Science* 253:323). These isoforms of APP are generated by alternative splicing of primary transcripts of a single gene, designated the APP gene, which is located on human chromosome 21. It is known that most of the APP isoforms are glycosylated transmembrane proteins (Goidgaber et al. (1987) *Science* 235:877), and that four of the isoforms, AA563, APP714, APP751 and APP770, have a protease inhibitor domain that is homologous to the Kunitz type of serine protease inhibitors. The β-amyloid (A4) segment comprises approximately half of the transmembrane domain and approximately the first 28 amino acids of the extracellular domain of an APP isoform.

Proteolytic processing of APP in vivo is a normal physiological process. Carboxy-terminal truncated forms of APP695, APP75 1, and APP770 are present in brain and cerebrospinal fluid (Palmert et al. (1989) *Proc. Natl. Acad. Sci. U.S.A.* 86:6338; Weidemann et al. (1989) *Cell* 57:115) and result from cleavage of the APP isoform at a constitutive cleavage site within the A4 peptide domain of an APP isoform (Esch et al. (1990) *Science* 248:1122). Normal proteolytic cleavage at the constitutive cleavage site yields a large (approximately 100 kD) soluble, N-terminal fragment that contains the protease inhibitor domain in some isoforms, and a 9–10 kD membrane-bound, C-terminal fragment that includes most of the A4 domain.

Generation of pathogenic β-amyloid (A4) protein appears to be the result of aberrant or alternative proteolytic processing of APP, such that normal cleavage at the constitutive site within the A4 domain does not occur, but rather cleavage occurs at two specific sites which flank the A4 domain. One of these aberrant cleavage sites is in the transmembrane domain and the other aberrant cleavage site is located approximately at the N-terminus of the first 28 amino acids of the extracellular domain (see FIG. 3). Such aberrant proteolytic cleavage produces the β-amyloid A4 polypeptide which is prone to forming dense amyloidogenic aggregates that are resistant to proteolytic degradation and removal. The resultant β-amyloid aggregates presumably are involved in the formation of the abundant amyloid plaques and cerebrovascular amyloid that are the neuropathological hallmarks of Alzheimer's disease. However, the exact aberrant cleavage sites are not always precise; β-amyloid molecules isolated from the brain of a patient with AD show N- and C-terminal heterogeneity. Therefore, the aberrant cleavage pathway may involve either sequence-specific proteolysis followed by exopeptidase activity (creating end-heterogeneity), or may not be sequence-specific.

The APP gene is known to be located on human chromosome 21. A locus segregating with familial Alzheimer's disease has been mapped to chromosome 21 (Hyslop et al. (1987) *Science* 235:885) close to the APP gene. Recombinants between the APP gene and the AD locus have been previously reported (Schellenberg et al. (1988) *Science* 241:1507). The data appeared to exclude the APP gene as the site of any mutation that might cause FAD (Van Broekhoven et al. (1987) *Nature* 329:153; Tanzi et al. (1987) *Nature* 329:156).

Recombinant DNA technology provides several techniques for analyzing genes to locate possible mutations. For example, the polymerase chain reaction (Bell (1989) *Immunology Today*, 10:351) may be used to amplify specific sequences using intronic primers, which can then be analyzed by direct sequencing.

Researchers working in the area of the hereditary cerebral haemorrhage with amyloidosis of the Dutch type ("HCHWA-D") (Levy et al. (1990) *Science* 248:11224) found a substitution of Glu to Gln at residue 618 (using the APP695 numbering system) in APP which is thought to result in the deposition of β-amyloid in the cerebral vessels of these patients. The present inventors have identified a single base substitution, a C to T transition at base pair 2149, has been found in part of the sequence of the APP gene in some cases of familial Alzheimer's disease. This base pair transition leads to an amino acid substitution, i.e., valine to isoleucine at amino acid 717 ($APP_{770}$) (see Yoshikai et al. (1990) *Gene* 87:257), close to the C-terminus of the β-amyloid protein. This suggests that some cases of Alzheimer's disease are caused by mutations in the APP gene, and specifically mutations that change codon 717 such that it encodes an amino acid other than valine.

Additionally, a further single base substitution, a T to G transition at adjacent base pair 2150, has been found in part of the sequence of the APP gene in other cases of familial Alzheimer's disease. This base pair transition leads to a different amino acid substitution, namely valine to glycine, at amino acid 717, thereby strengthening the argument that some cases of Alzheimer's disease are caused by mutations in the APP gene, specifically at codon 717.

It is now clear that a mutation in the APP gene locus that results in a substitution of isoleucine for valine at codon 717 (residue 642 in APP695) gives rise to AD in some families (Goate et al. (1991) *Nature* 349:704). A second APP allelic variant wherein glycine is substituted for valine at codon 717 is now identified, and is so closely linked to the AD phenotype as to indicate that allelic variants at codon 717 of the APP gene, particularly those encoding an amino acid other than valine, and more particularly those encoding a isoleucine, glycine, or phenylalanine, are pathogenic and/or pathognomonic alleles (Chartier-Harlin et al. (1991) *Nature* 353:844).

Proteolysis on either side of the β-amyloid (A4) region of APP may be enhanced or qualitatively altered by the specific mutations at codon 717, increasing the rate of β-amyloid deposition and aggregation. Such codon 717 mutations may increase β-amyloid formation by providing a poorer substrate for the main proteolytic pathway (cleavage at the constitutive site) or a better substrate for a competing, alternative cleavage pathway (at aberrant cleavage sites).

DEFINITIONS

A number of terms and expressions are used throughout the specification and, to facilitate the understanding thereof, the following definitions are provided:

As used herein, "exon" refers to any segment of an interrupted gene that is represented in the mature RNA product.

As used herein, "intron" refers to a segment of an interrupted gene that is not represented in the mature RNA product. Introns are part of the primary nuclear transcript but are spliced out to produce mRNA, which is then transported to the cytoplasm.

As used herein, the phrase "gene sequence coding for amyloid protein precursor" may be interpreted to mean the DNA and cDNA sequence as detailed by Yoshikai et al. (1990) *Gene* 87:257 and Kang et al, loc. cit., together with the promoter DNA sequence as described by Salbaum et al. (1988) *EMBO* 7(9):2807.

As used herein, the terms "label" or "labeled" refers to incorporation of a detectable marker (e.g., by incorporation of a radiolabeled nucleotide or by end-labeling with a terminal radiolabeled phosphate). DNA or RNA is typically labeled by incorporation of a radiolabeled nucleotide ($H^3$, $C^{14}$, $S^{35}$, $P^{32}$) or a biotinylated nucleotide that can be detected by marked avidin (e.g., avidin containing a fluorescent marker or enzymatic activity) or digoxygeninylated nucleotide that can be detected by marked specific antibody.

As used herein, "isoform", "APP", and "APP isoform" refer to a polypeptide that is encoded by at least one exon of the APP gene (Kitaguchi et al. (1988) *Nature* 331:530; Ponte et al., ibid., p.525; R. E. Tanzi, ibid., p.528; de Sauvage and Octave (1989) *Science* 245:651; Golde et al. (1990) *Neuron* 4:253). An APP isoform may be encoded by an APP allele (or exon thereof) that is associated with a form of Alzheimer's disease or that is not associated with an AD disease phenotype.

The term "β-amyloid gene" is used herein as a synonym for the APP gene, as β-amyloid is a protein product produced by a post-translational cleavage of an APP gene product.

As used herein, "fragment" refers to a polypeptide of at least about 9 amino acids, typically 50 to 75, or more, wherein the polypeptide contains an amino acid core sequence (listed in order from amino- to carboxy-terminal direction):

-Ile-Ala-Thr-Val-Ile-X-Ile-Thr-Leu- [SEQ ID NO:6]

where X is any of the twenty conventional amino acids except valine, and particularly where X is isoleucine, glycine, or phenylalanine. A fragment may be a truncated APP isoform, modified APP isoform (as by amino acid substitutions, deletions, or additions outside of the core sequence), or other variant polypeptide sequence, but is not a naturally-occurring APP isoform or β-amyloid polypeptide that is present in a human individual, whether affected by AD or not. If desired, the fragment may be fused at either terminus to additional amino acids, which may number from 1 to 20, typically 50 to 100, but up to 250 to 500 or more.

As used herein, "APP751" and "APP770" refer, respectively, to the 751 and 770 amino acid residue long polypeptides encoded by the human APP gene (Ponte et al. loc. cit.; Kitaguchi et al. loc. cit.; Tanzi et al. loc. cit.).

As used herein, "codon 717" refers to the codon (i.e., the trinucleotide sequence) that encodes the 717th amino acid position in APP770, or the amino acid position in an APP isoform or fragment that corresponds to the 717th position in APP770. For example but not limitation, a 670 residue long fragment that is produced by truncating APP770 by removing the 100 N-terminal amino acids has its 617th amino acid position corresponding to codon 717. In fact, as used herein, codon 717 refers to the codon that encodes the 698th amino acid residue of APP751 [SEQ ID NO:2] and the 642nd amino acid residue of APP695 [SEQ ID NO:1].

As used herein, "human APP isoform or fragment" refers to an APP isoform or fragment that contains a sequence of at least 9 consecutive amino acids that is identical to a sequence in a human APP770, APP751, or APP695 protein that occurs naturally in a human individual, and wherein an identical sequence is not present in an APP protein that occurs naturally in a nonhuman species.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame.

The term "corresponds to" is used herein to mean that a sequence is homologous (i.e., is identical, not strictly evolutionarily related) to all or a portion of a reference sequence. In contradistinction, the term "complementary to" is used herein to mean that the complementary sequence is homologous to all or a portion of a reference sequence. For illustration, the nucleotide sequence "TATAC" corresponds to a reference sequence "TATAC" and is complementary to a reference sequence "GTATA".

The term "transcriptional enhancement" is used herein to refer to functional property of producing an increase in the rate of transcription of linked sequences that contain a functional promoter.

The term "agent" is used herein to denote a chemical compound, a mixture of chemical compounds, a biological macromolecule, or an extract made from biological materials such as bacteria, plants, fungi, or animal (particularly mammalian) cells or tissues. Agents are evaluated for potential biological activity by inclusion in screening assays described hereinbelow.

As used herein, the term "mutant" refers to APP alleles having missense mutations that are pathognomonic for a genetic predisposition for developing AD; specifically a mutation at codon 717 (as referenced by the amino acid sequence in APP770) of the APP gene, such that codon 717 encodes one of the nineteen amino acids that are not valine (i.e., glycine, methionine, alanine, serine, isoleucine, leucine, threonine, proline, histidine, cysteine, tyrosine, phenylalanine, glutamic acid, tryptophan, arginine, aspartic acid, asparagine, lysine and glutamine), but preferably isoleucine, glycine, or phenylalanine. Thus a mutant APP770 polypeptide is an APP770 polypeptide that has an amino acid residue at position 717 that is not valine. Other mutant APP isoforms comprise a non-valine amino acid at the amino acid residue position that corresponds to codon 717 (i.e., that is encoded by codon 717). Similarly, a mutant APP allele or a variant APP codon 717 allele is an APP allele that encodes an amino acid other than valine at codon 717 (referenced to the human APP770 deduced translation as described in the "codon 717" definition, supra), preferably isoleucine, glycine, or phenylalanine. Hence, an APP allele that encodes valine at codon 717 is a "wild-type" APP allele.

It is apparent to one of skill in the art that nucleotide substitutions, deletions, and additions may be incorporated into the polynucleotides of the invention. However, such nucleotide substitutions, deletions, and additions should not substantially disrupt the ability of the polynucleotide to hybridize to one of the polynucleotide sequences shown in FIGS. 5 and 6 under hybridization conditions that are sufficiently stringent to result in specific hybridization.

"Specific hybridization" is defined herein as the formation of hybrids between a probe polynucleotide (e.g., a polynucleotide of the invention which may include substitutions, deletion, and/or additions) and a specific target polynucleotide (e.g., a polynucleotide having the sequence ), wherein the probe preferentially hybridizes to the specific target such that, for example, a band corresponding to a variant APP allele or restriction fragment thereof, can be identified on a Southern blot, whereas a corresponding wild-type APP allele (i.e., one that encodes valine at codon 717) is not identified or can be discriminated from a variant APP allele on the basis of signal intensity. Hybridization probes capable of specific hybridization to detect a single-base mismatch may be designed according to methods known in the art and described in Maniatis et al., *Molecular Cloning: A Laboratory Manual*, 2nd Ed., (1989), Cold Spring Harbor, N.Y. and Berger and Kimmel, *Methods in Enzymology*, Volume 152, *Guide to Molecular Cloning Techniques* (1987), Academic Press, Inc., San Diego, Calif.; Gibbs et al. (1989) *Nucleic Acids Res.* 17:2437; Kwok et al. (1990) *Nucleic Acids Res.* 18:999; Miyada et al. (1987) *Methods Enzymol.* 154:94, each of which is incorporated herein by reference. The $T_m$ for oligonucleotides is calculated under standard conditions (1 M NaCl) to be [4° C.×(G+C)+2° C.×(A+T)]. While the conditions of PCR differ from the standard conditions, this $T_m$ is used as a guide for the expected relative stabilities of oligonucleotides. Allele-specific primers are typically 13–15 nucleotides long, sometimes 16–21 nucleotides long, or longer; when short primers are used, such as a 14 nucleotide long primer, low annealing temperatures are used, typically 44 to 50° C., occasionally somewhat higher or lower depending on the base composition of the sequence(s).

DESCRIPTION OF THE PREFERRED EMBODIMENTS

Detection of Mutant Codon 717 APP Alleles

In an embodiment of the invention, the method involves identifying a genetic alteration at amino acid 717, which may cause the consensus Val to be changed, for example, to another hydrophobic residue. This will generally be performed on a specimen removed from the subject. Hydrophobic residues include Leu, Ala, Ile and Gly, the first three of which have aliphatic side chains. Phe also has a hydrophobic residue which may be appropriate. As indicated above, preferred residues include Ile, Gly, and Phe (Murrell et al, (1991) *Science* 254:97).

The fact that these mutations discussed above are at the same codon may be a coincidence, but this seems unlikely on statistical grounds. There are two possibilities that may explain these data. First, substitution of the valine residue at codon 717 may result in increased beta-amyloid deposition due to changes in APP metabolism. Secondly, the variation in the sequence around this position may result in increased translation of APP mRNAs and thus cause AD by a route analogous to that by which AD is believed to be caused in Down Syndrome (Tanzi and Hyman (1991) *Nature* 350:564 and Rumble et al. (1989) *N. Engl. J. Med.* 320:1446). In situ hybridization studies have shown that APP 717 mutations do not alter APP expression (Harrison et al. (1991) *Neurorep.* 2:152).

The V717I (APP 717 Val→Ile), V717G (APP 717 Val→Gly) and V717F (APP 717 Val→Phe) mutations would destabilise a putative stem loop structure and destroy a possible iron-responsive element between base pairs 2131 and 2156 (Tanzi and Hyman, loc. cit.). There are several other possible mutations which could also disrupt this structure, many of which would be silent at the protein level; yet these mutations specifically referred to have involved a change to the same amino acid, and no silent changes or changes to other amino acids have been reported prior to the work described herein. Examination of sequence data from 10 other mammalian species (Johnstone et al. (1991) *Mol. Brain Res.* 10:299) shows that while the valine residue at codon 717 is conserved in all of them, the putative stem loop structure postulated from the human sequence (Tanzi and Hyman loc. cit.) would not be predicted to occur in either cattle or sheep; and in pig and mouse the consensus sequence for the iron-responsive elements is not present. Finally, such stem loop structures are believed to modulate gene translation by altering mRNA stability (Klausner and Harford (1989) *Science* 246:870); however, Harrison and colleagues (Harrison et al. loc. cit.) have shown by in situ hybridization that APP mRNAs are not grossly altered in the brain of an individual with the V717I mutation. For these reasons, it is believed likely that alterations in the rate of APP translation caused by the specific mutations identified are not likely to be the key to their pathogenicity.

The fact that the specific mutations discussed involve different changes (Val→Ile, Val→Gly, and Val→Phe) suggests that neither side-chain hydrophobicity nor side-chain bulk is the crucial issue. All examples of APP alleles that encode an amino acid other than valine at codon 717, cosegregate with FAD; suggesting that the valine that occurs at position 717 in wild-type APP770 or APP751 is a critical amino acid residue for non-pathogenic APP proteolytic processing (i.e., by the constitutive cleavage pathway).

The major metabolic pathway for the APP molecule involves cleavage within the beta-amyloid fragment (Esch et al. loc. cit.). To generate beta-amyloid, there must be a second pathway in which APP is cleaved outside this sequence. Such a cleavage would be likely to leave a stub of the APP molecule containing the beta-amyloid fragment embedded in the membrane. Possibly, the beta-amyloid-containing fragment which is generated by the second pathway is degraded by peptidase action; the reported mutations may be pathogenic because peptides which contain them may be more resistant to the actions of this peptidase. Therefore, genetic alterations in the APP gene which result in altered (generally reduced) degradative properties are particularly important in the application of the invention. There are several methodologies available from recombinant DNA technology which may be used for detecting and identifying a genetic mutation responsible for Alzheimer's disease. These include direct probing, polymerase chain reaction (PCR) methodology, restriction fragment length polymorphism (RFLP) analysis and single strand conformational analysis (SSCA).

Detection of point mutations using direct probing involves the use oligonucleotide probes which may be prepared synthetically or by nick translation. The DNA probes may be suitably labelled using, for example, a radiolabel, enzyme label, fluorescent label, biotin-avidin label and the like for subsequent visualization in for example a Southern blot hybridization procedure. The labelled probe is reacted with the sample DNA bound to a nitrocellulose or Nylon 66 substrate. The areas that carry DNA sequences complementary to the labelled DNA probe become labelled themselves as a consequence of the reanealling reaction. The areas of the filter that exhibit such labelling may then be visualized, for example, by autoradiography.

Alternative probing techniques, such as ligase chain reaction (LCR) involve the use of mismatch probes, i.e., probes which have full complementarity with the target except at the point of the mutation. The target sequence is then allowed to hybridize both with oligonucleotides having full complementarity and oligonucleotides containing a mismatch, under conditions which will distinguish between the two. By manipulating the reaction conditions it is possible to obtain hybridization only where there is full complementarity. If a mismatch is present then there is significantly reduced hybridization.

The polymerase chain reaction (PCR) is a technique that amplifies specific DNA sequences with remarkable efficiency. Repeated cycles of denaturation, primer annealing and extension carried out with a heat stable enzyme Taq polymerase leads to exponential increases in the concentration of desired DNA sequences.

Given a knowledge of the nucleotide sequence encoding the precursor of amyloid protein of AD (Kang et al. loc. cit., and Yoshikai, above) it may be possible to prepare synthetic oligonucleotides complementary to sequences which flank the DNA of interest. Each oligonucleotide is complementary to one of the two strands. The DNA is then denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million fold can be achieved. The resulting DNA may then be directly sequenced in order to locate any genetic alteration. Alternatively, it may be possible to prepare oligonucleotides that will only bind to altered DNA, so that PCR will only result in multiplication of the DNA if the mutation is present. Following PCR, allele-specific oligonucleotide hybridization (Dihella et al. (1988) *Lancet* 1:497) may be used to detect the AD point mutation. Alternatively an adaptation of PCR called amplification of specific alleles (PASA) can be employed; this uses differential amplification for rapid and reliable distinction between alleles that differ at a single base pair.

In yet another method PCR may be followed by restriction endonuclease digestion with subsequent analysis of the resultant products. The substitution of T for C at base pair 2149, found as a result of sequencing exon 17, creates a BclI restriction site. The creation of this restriction endonuclease recognition site facilitates the detection of the AD mutation using RFLP analysis or by detection of the presence or absence of a polymorphic BclI site in a PCR product that spans codon 717.

For RFLP analysis, DNA is obtained, for example, from the blood of the subject suspected of having AD and from a normal subject is digested with the restriction endonuclease BclI and subsequently separated on the basis of size using agarose gel electrophoresis. The Southern blot technique can then be used to detect, by hybridization with labeled probes, the products of endonuclease digestion. The patterns obtained from the Southern blot can then be compared. Using such an approach, DNA spanning an Alzheimer's mutation that creates or removes a restriction site at codon 717, such as the BclI site, is detected by determining the number of bands detected and comparing this number to a reference allele that has a codon 717 allele that encodes valine.

Correspondingly, the substitution of G for T at base pair 2150 creates a SfaNI restriction site (GCATC), which may be exploited in a manner similar to that described above, mutans mutandis. Similar creation of additional restriction sites by nucleotide substitutions within codon 717, wherein the codon 717 encodes an amino acid other than valine, can be readily calculated by reference to the genetic code and a list of nucleotide sequences recognized by restriction endonucleases (*Promega Protocols and Applications Guide*, (1991) Promega Corporation, Madison, Wis.).

Single strand conformational analysis (SSCA) (Orita et al. (1989) *Genomics* 5:874 and Orita et al. (1990) *Genomics* 6:271) offers a relatively quick method of detecting sequence changes which may be appropriate in at least some instances.

PCR amplification of specific alleles (PASA) is a rapid method of detecting single-base mutations or polymorphisms (Newton et al. (1989) *Nucleic Acids Res.* 17:2503; Nichols et al. (1989) *Genomics* 5:535; Okayama et al. (1989) *J. Lab. Clin. Med.* 114: 105; Sarkar et al. (1990) *Anal. Biochem.* 186:64; Sommer et al. (1989) *Mayo Clin. Proc.* 64:1361; Wu (1989) *Proc. Natl. Acad. Sci. U.S.A.* 86:2757; and Dutton et al. (1991) *Biotechniques* 11:700). PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify one or more variant APP codon 717 alleles. Where such amplification is done on genetic material (or RNA) obtained from an individual, it can serve as a method of detecting the presence of one or more variant APP codon 717 alleles in an individual.

Similarly, a method known a ligase chain reaction (LCR) has been used to successfully detect a single-base substitution in a hemoglobin allele that causes sickle cell anemia (Barany et al. (1991) *Proc. Natl. Acad. Sci. U.S.A.* 88:189; Weiss (1991) *Science* 254:1292). LCR probes may be combined, or multiplexed for simultaneously screening for multiple different mutations. Thus, one method of screening for variant APP codon 717 alleles is to multiplex at least two, and preferably all, LCR probes that will detect an APP allele having a codon 717 that does not encode valine, but that does encode an amino acid. The universal genetic code provides the degenerate sequences of all the encoded non-valine amino acids, thus LCR probe design for detecting any particular variant codon 717 allele is straightforward, and multiplexed pools of such LCR probes may be selected in the discretion of a practitioner for his particular desired use.

In performing diagnosis using any of the above techniques or variations thereof, it is preferable that several individuals are examined. These may include an unaffected parent, an affected parent, an affected sibling, an unaffected sibling as well as other perhaps more distant family members.

Model Animals and Cell Lines

Having identified specific mutations in codon 717 of the β-amyloid gene as a cause of familial Alzheimer's disease (FAD), it is possible, using genetic manipulation, to develop transgenic model systems and/or whole cell systems containing the mutated FAD gene (or a portion thereof) for use, for example, as model systems for screening for drugs and evaluating drug effectiveness. Additionally, such model systems provide a tool for defining the underlying biochemistry of APP and β-amyloid metabolism, which thereby provides a basis for rational drug design.

One type of cell system can be naturally derived. For this, blood samples from the affected subject must be obtained in order to provide the necessary cells which can be permanently transformed into a lymphoblastoid cell line using, for example, Epstein-Barr virus.

Once established, such cell lines can be grown continuously in suspension culture and may be used for a variety of in vitro experiments to study APP expression and processing.

Since the FAD mutation is dominant, an alternative method for constructing a cell line is to engineer genetically a mutated gene, or a portion thereof spanning codon 717, into an established (either stably or transiently) cell line of choice. Sisodia (1990) *Science* 248:492) has described the insertion of a normal APP gene, by transfection, into mammalian cells. Oltersdorf et al. ((1990) *J. Biol. Chem.* 265:4492) describe the insertion of APP into immortalized eukaryotic cell lines.

Baculovirus expression systems are useful for high level expression of heterologous genes in eukaryotic cells. Knops et al. (1991) *J. Biol. Chem.* 266(11):7285 describes the expression of APP using such a system.

In yet a further use of the present method, it may be possible to excise the mutated gene (i.e., a variant APP codon 717 gene) for use in the creation of transgenic animals containing the mutated gene. For example, an entire human variant APP codon 717 allele may be cloned and isolated, either in parts or as a whole, in a cloning vector (e.g., λCharon35, cosmid, or yeast artificial chromosome). The human variant APP codon 717 gene, either in parts or in whole, may be transferred to a host nonhuman animal, such as a mouse. As a result of the transfer, the resultant transgenic nonhuman animal will preferably express one or more variant APP codon 717 polypeptides. Most preferably, a transgenic nonhuman animal of the invention will express one or more variant APP codon 717 polypeptides in a neuron-specific manner (Wirak et al. (1991) *EMBO* 10:289). This may be accomplished by transferring substantially the entire human APP gene (encoding a codon 717 mutant) including the 4.5 kilobase sequence that is adjacent to and upstream of the first major APP transcriptional start site.

Alternatively, one may design minigenes encoding variant APP codon 717 polypeptides. Such minigenes may contain a CDNA sequence encoding a variant APP codon 717 polypeptide, preferably full-length, a combination of APP gene exons, or a combination thereof, linked to a downstream polyadenylation signal sequence and an upstream promoter (and preferably enhancer). Such a minigene construct will, when introduced into an appropriate transgenic host (e.g., mouse or rat), express an encoded variant APP codon 717 polypeptide, most preferably a variant APP codon 717 polypeptide that contains either an isoleucine, glycine, or phenylalanine residue at codon 717 of APP770 or the corresponding position in an APP isoform or fragment.

One approach to creating transgenic animals is to target a mutation to the desired gene by homologous recombination in an embryonic stem (ES) cell line in vitro followed by microinjection of the modified ES cell line into a host blastocyst and subsequent incubation in a foster mother (see Frohman and Martin (1989) *Cell* 56:145). Alternatively, the technique of microinjection of the mutated gene, or a portion thereof, into a one-cell embryo followed by incubation in a foster mother can be used. Various uses of transgenic animals, particularly transgenic animals that express a wild-type APP isoform or fragment, are disclosed in Wirak et al. (1991) *EMBO*, 10(2):289; Schilling et al. (1991) *Gene* 98(2):225; Quon et al. (1991) *Nature* 352:239; Wirak et al. (1991) *Science* 253:323; and Kawabata et al. (1991) *Nature* 354:476. Additional methods for producing transgenic animals are known in the art.

Alternatively, site-directed mutagenesis and/or gene conversion can be used to mutate a murine (or other nonhuman) APP gene allele, either endogenous or transfected, such that the mutated allele does not encode valine at the codon position in the mouse APP gene that corresponds to codon 717 (of APP770) of the human APP gene (such position is readily identified by homology matching of the murine APP gene or APP protein to the human APP gene or APP770 protein). Preferably, such a mutated murine allele would encode isoleucine or glycine or phenylalanine at the corresponding codon position.

Therapeutics

Having detected the genetic mutation in the gene sequence coding for β-amyloid protein in an individual not yet showing overt signs of familial AD, using the method of the present invention, it may be possible to employ gene therapy, in the form of gene implants, to prevent the development of the disease.

Additional embodiments directed to modulation of the production of variant APP proteins include methods that employ specific antisense polynucleotides complementary to all or part of a variant APP sequence, or for some embodiments a wild-type APP sequence. Such complementary antisense polynucleotides may include nucleotide substitutions, additions, deletions, or transpositions, so long as specific hybridization to the relevant target sequence, i.e., a variant APP codon 717 sequence, is retained as a property of the polynucleotide. Thus, an antisense polynucleotide must preferentially bind to a variant APP (i.e., codon 717 does not encode valine) sequence as compared to a wild-type APP (i.e., codon 717 does encode valine). It is evident that the antisense polynucleotide must reflect the exact nucleotide sequence of the variant allele (or wild-type allele where desired) and not a degenerate sequence.

Complementary antisense polynucleotides include soluble antisense RNA or DNA oligonucleotides which can hybridize specifically to a variant APP MRNA species and prevent transcription of the mRNA species and/or translation of the encoded polypeptide (Ching et al. (1989) *Proc. Natl. Acad. Sci. U.S.A.* 86:10006; Broder et al. (1990) *Ann. Int. Med.* 113:604; Loreau et al. (1990) *FEBS Letters* 274:53–56); Holcenberg et al. WO91/11535; U.S. Pat. No. 7,530,165 ("New human CRIPTO gene"—publicly available through Derwent Publications Ltd., Rochdale House, 128 Theobalds Road, London, UK); WO91/09865; WO91/04753; WO90/13641; and EP 386563, each of which is incorporated herein by reference). The antisense polynucleotides therefore inhibit production of the variant APP polypeptides. Antisense polynucleotides may preferentially inhibit transcription and/or translation of mRNA corresponding to a variant (or wild-type) polypeptides can inhibit T lymphocyte activation.

Antisense polynucleotides may be produced from a heterologous expression cassette in a transfectant cell or transgenic cell or animal, such as a transgenic neural, glial, or astrocytic cell, preferably where the expression cassette contains a sequence that promotes cell-type specific expression (Wirak et al. loc. cit.). Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA*, (1988), D. A. Melton, Ed., Cold Spring Harbor Laboratory, Cold Spring Harbor, N.Y.).

Mutant APP Antigens and Monoclonal Antibodies

In yet another aspect of the invention, having detected a genetic alteration in a gene sequence coding for APP, it may be possible to obtain samples of the altered β-amyloid protein from the same source. This protein may be derived from the brain tissue of a subject diagnosed as suffering from Alzheimer's disease, or more preferably are produced by recombinant DNA methods or are synthesized by direct chemical synthesis on a solid support. Such polypeptides will contain an amino acid sequence of an APP variant allele spanning codon 717. Examples of such sequences are:

(a) -Ile-Ala-Thr-Val-Ile-Gly-Ile-Thr-Leu- [SEQ ID NO:7]

(b) -Ile-Ala-Thr-Val-Ile-Met-Ile-Thr-Leu- [SEQ ID NO:8]

(c) -Ile-Ala-Thr-Val-Ile-Ala-Ile-Thr-Leu- [SEQ ID NO:9]

(d) -Ile-Ala-Thr-Val-Ile-Ser-Ile-Thr-Leu- [SEQ ID NO:10]

(e) -Ile-Ala-Thr-Val-Ile-Ile-Ile-Thr-Leu- [SEQ ID NO:11]

(f) -Ile-Ala-Thr-Val-Ile-Leu-Ile-Thr-Leu- [SEQ ID NO:12]

(g) -Ile-Ala-Thr-Val-Ile-Thr-Ile-Thr-Leu- [SEQ ID NO:13]

(h) -Ile-Ala-Thr-Val-Ile-Pro-Ile-Thr-Leu- [SEQ ID NO:14]

(i) -Ile-Ala-Thr-Val-Ile-His-Ile-Thr-Leu- [SEQ ID NO:15]

(j) -Ile-Ala-Thr-Val-Ile-Cys-Ile-Thr-Leu- [SEQ ID NO:16]

(k) -Ile-Ala-Thr-Val-Ile-Tyr-Ile-Thr-Leu- [SEQ ID NO:17]

(l) -Ile-Ala-Thr-Val-Ile-Phe-Ile-Thr-Leu- [SEQ ID NO:18]

(m) -Ile-Ala-Thr-Val-Ile-Glu-Ile-Thr-Leu- [SEQ ID NO:19]

(n) -Ile-Ala-Thr-Val-Ile-Trp-Ile-Thr-Leu- [SEQ ID NO:20]

(o) -Ile-Ala-Thr-Val-Ile-Arg-Ile-Thr-Leu- [SEQ ID NO:21]

(p) -Ile-Ala-Thr-Val-Ile-Asp-Ile-Thr-Leu- [SEQ ID NO:22]

(q) -Ile-Ala-Thr-Val-Ile-Asn-Ile-Thr-Leu- [SEQ ID NO:23]

(r) -Ile-Ala-Thr-Val-Ile-Lys-Ile-Thr-Leu- [SEQ ID NO:24]

(s) -Ile-Ala-Thr-Val-Ile-Gln-Ile-Thr-Leu- [SEQ ID NO:25]

Using such polypeptide material it may then be possible to prepare antisera and monoclonal antibodies using, for example, the method of Kohler and Milstein ((1975) *Nature* 256:495). Such monoclonal antibodies could then form the basis of a diagnostic test.

Such variant APP polypeptides may be used to immunize an animal for the production of specific antibodies. These antibodies may comprise a polyclonal antiserum or may comprise a monoclonal antibody produced by hybridoma cells. For general methods to prepare antibodies, see *Antibodies: A Laboratory Manual*, (1988) E. Harlow and D. Lane, Cold Spring Harbor Laboratory, Cold Spring Harbor, N.Y., which is incorporated herein by reference.

For example but not for limitation, a recombinantly produced fragment of a variant APP codon 717 polypeptide can be injected into a mouse along with an adjuvant so as to generate an immune response. Murine immunoglobulins which bind the recombinant fragment with a binding affinity of at least $1 \times 10^7$ M$^{-1}$ can be harvested from the immunized mouse as an antiserum, and may be further purified by affinity chromatography or other means. Additionally, spleen cells are harvested from the mouse and fused to myeloma cells to produce a bank of antibody-secreting hybridoma cells. The bank of hybridomas can be screened for clones that secrete immunoglobulins which bind the recombinantly produced fragment with an affinity of at least $1 \times 10^6$ M$^{-1}$. More specifically, immunoglobulins that bind to the variant APP codon 717 polypeptide but have limited crossreactivity with a wild-type (i.e., codon 717 encodes valine) APP polypeptide are selected, either by preabsorption with wild-type APP or by screening of hybridoma cell lines for specific idiotypes that preferentially bind the variant as compared to the wild-type.

The nucleic acid sequences of the present invention capable of ultimately expressing the desired variant APP polypeptides can be formed from a variety of different polynucleotides (genomic or cDNA, RNA, synthetic oligonucleotides, etc.) as well as by a variety of different techniques.

As stated previously, the DNA sequences will be expressed in hosts after the sequences have been operably linked to (i.e, positioned to ensure the functioning of) an expression control sequence. These expression vectors are typically replicable in the host organisms either as episomes or as an integral part of the host chromosomal DNA. Commonly, expression vectors will contain selection markers, e.g., tetracycline resistance or hygromycin resistance, to permit detection and/or selection of those cells transformed with the desired DNA sequences (see, e.g., U.S. Pat. No. 4,704,362, which is incorporated herein by reference).

Polynucleotides encoding a variant APP codon 717 polypeptide may include sequences that facilitate transcription (expression sequences) and translation of the coding sequences, such that the encoded polypeptide product is produced. Construction of such polynucleotides is well known in the art and is described further in Maniatis et al. *Molecular Cloning: A Laboratory Manual*, 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

*E. coli* is one prokaryotic host useful particularly for cloning the DNA sequences of the present invention. Other microbial hosts suitable for use include bacilli, such as *Bacillus subtilus*, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "From Genes to Clones," VCH Publishers, New York, N.Y. (1987), which is incorporated herein by reference). Eukaryotic cells are actually preferred, because a number of suitable host cell lines capable of secreting intact human proteins have been developed in the art, and include the CHO cell lines, various COS cell lines, HeLa cells, myeloma cell lines, Jurkat cells, etc. Expression vectors for these cells can include expression control sequences, such as an origin of replication, a promoter, an enhancer (Queen et al. (1986) *Immunol. Rev.* 89:49, which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, and the like. The vectors containing the DNA segments of interest (e.g., polypeptides encoding a variant APP polypeptide) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, generally, Maniatis, et al. *Molecular Cloning: A Laboratory Manual*, Cold Spring Harbor Press, (1982), which is incorporated herein by reference.)

Alternatively, homologous recombination may be used to insert an APP mutant sequence into a host genome at a specific site, for example, at a host APP locus. In one type of homologous recombination, one or more host sequence(s) are replaced; for example, a host APP allele (or portion thereof) is replaced with a mutant APP allele (or portion thereof). In addition to such gene replacement methods, homologous recombination may be used to target a mutant APP allele to a specific site other than a host APP locus. Homologous recombination may be used to produce transgenic non-human animals and/or cells that incorporate mutant APP alleles.

The method lends itself readily to the formulation of test kits which can be utilized in diagnosis. Such a kit would comprise a carrier being compartmentalized to receive in close confinement one or more containers wherein a first container may contain suitably labelled DNA probes. Other containers may contain reagents useful in the localization of the labelled probes, such as enzyme substrates. Still other containers may contain a restriction enzyme (such as BclI), buffers and the like, together with instructions for use.

EXPERIMENTAL EXAMPLES

The following examples are provided for illustration and are not intended to limit the invention to the specific example provided.

Example 1

Detection of a Val→Ile mutation in the β-amyloid (APP) gene

The segregation of AD and markers along the long arm of chromosome 21 in a single family with autopsy-confirmed Alzheimer's disease (see FIG. 1) were examined. DNA samples were available from a total of six affected and 33 unaffected and at risk individuals.

Figure 2:
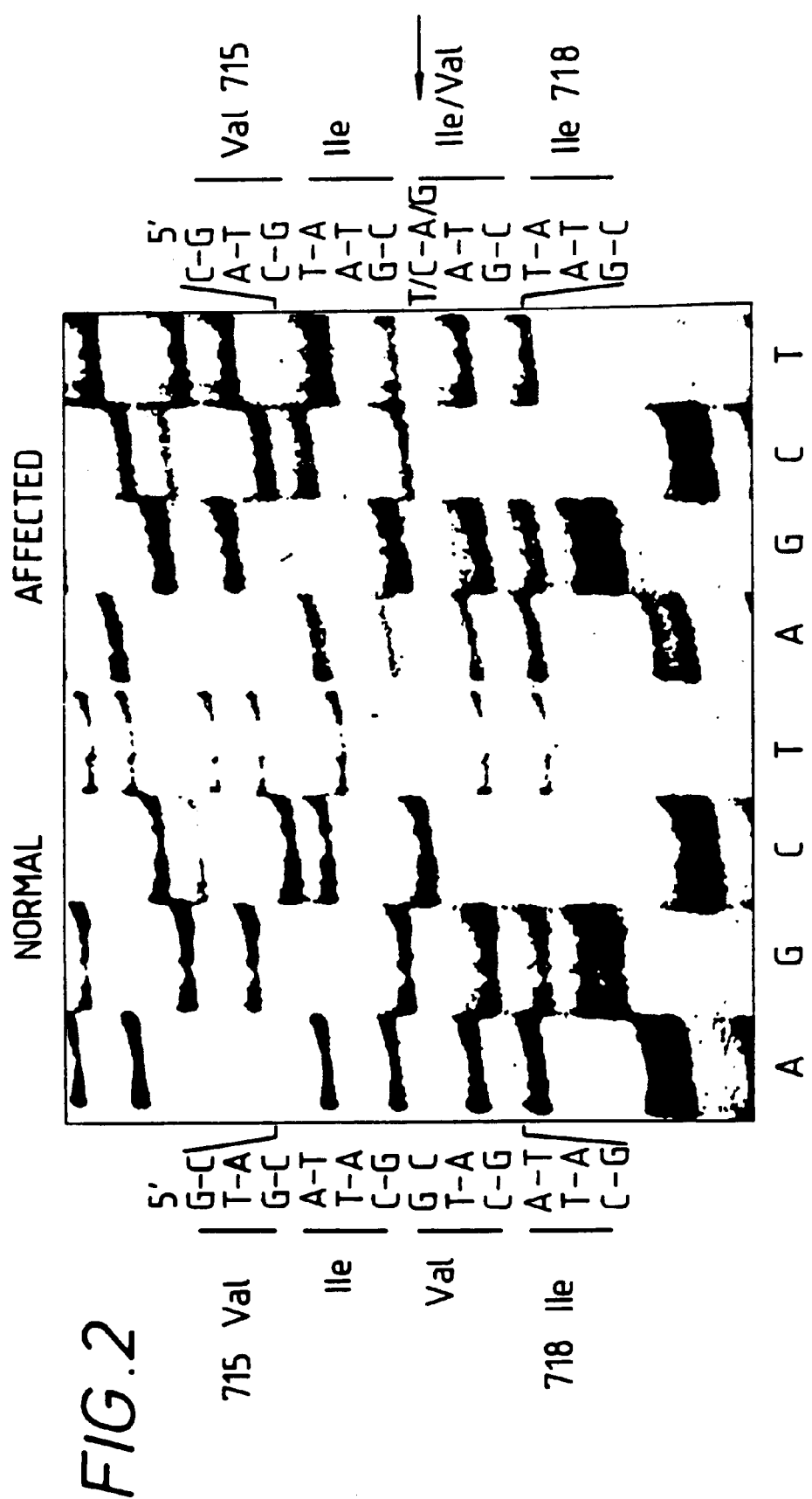
FIG. 2 shows an autoradiograph of a sequencing gel from part of exon 17 of the APP gene in a normal and an affected individual from the FIG. 1 pedigree showing a single base pair change at base pair 2149 in the affected individual. This C to T transition leads to an amino acid substitution of a valine by an isoleucine at codon 717.

The APP gene in an affected family member was analyzed by polymerase chain reaction (PCR) direct sequencing using intronic primers (Gyllensten, U. in PCR Technology, Ed. Erlich, H. A., Stockton Press, 45–60, 1989; Yoshikai et al. (1990) *Gene* 87:257). (FIG. 2). The primers were made according to the manufacturer's protocol using a Gene Assembler Plus (Pharmacia LKB).

PCR was carried out using the following intronic primers in order to amplify exon 17 of the APP gene:

[A] 5'-CCTCATCCAAATGTCCCCGTCATT-3' [SEQ ID NO:26] AND

[B] 5'-GCCTAATTCTCTCATAGTCTTAATTCCCAC-3' [SEQ ID NO 27]

PCR conditions were 94° C. for 10 min to denature; then 35 cycles of 60° C. for 1 min, 72° C. for 3 min, 94° C. for 1.5 min; and a single cycle of 72° C. for 10 min. The reaction was carried out using 10 mM tris-HCl pH 8.3, 50 mM potassium chloride, 0.01% gelatin, 1.5 mM magnesium chloride, 200 μM of dNTPs, 50 pmoles of each PCR primer and 1 unit of Taq polymerase. The total final reaction volume was 25 μl.

A second PCR reaction was then performed with a final concentration of 50 pmol of primer [A] and 0.5 pmol of primer [B]. The PCR product was purified on a centricon 100 microconcentrator (Amicon) and used directly for sequencing with the SEQUENASE kit (version 2.0, United States Biochemical Corp.; the word SEQUENASE is a trade mark) following the manufacturer's protocol.

Exon 17 was sequenced first because it encodes part of the β-amyloid peptide and is the site of the mutation (at APP693) leading to Hereditary Cerebral Haemorrhage with Amyloidosis-Dutch Type (HCHWA-D).

Figure 3:
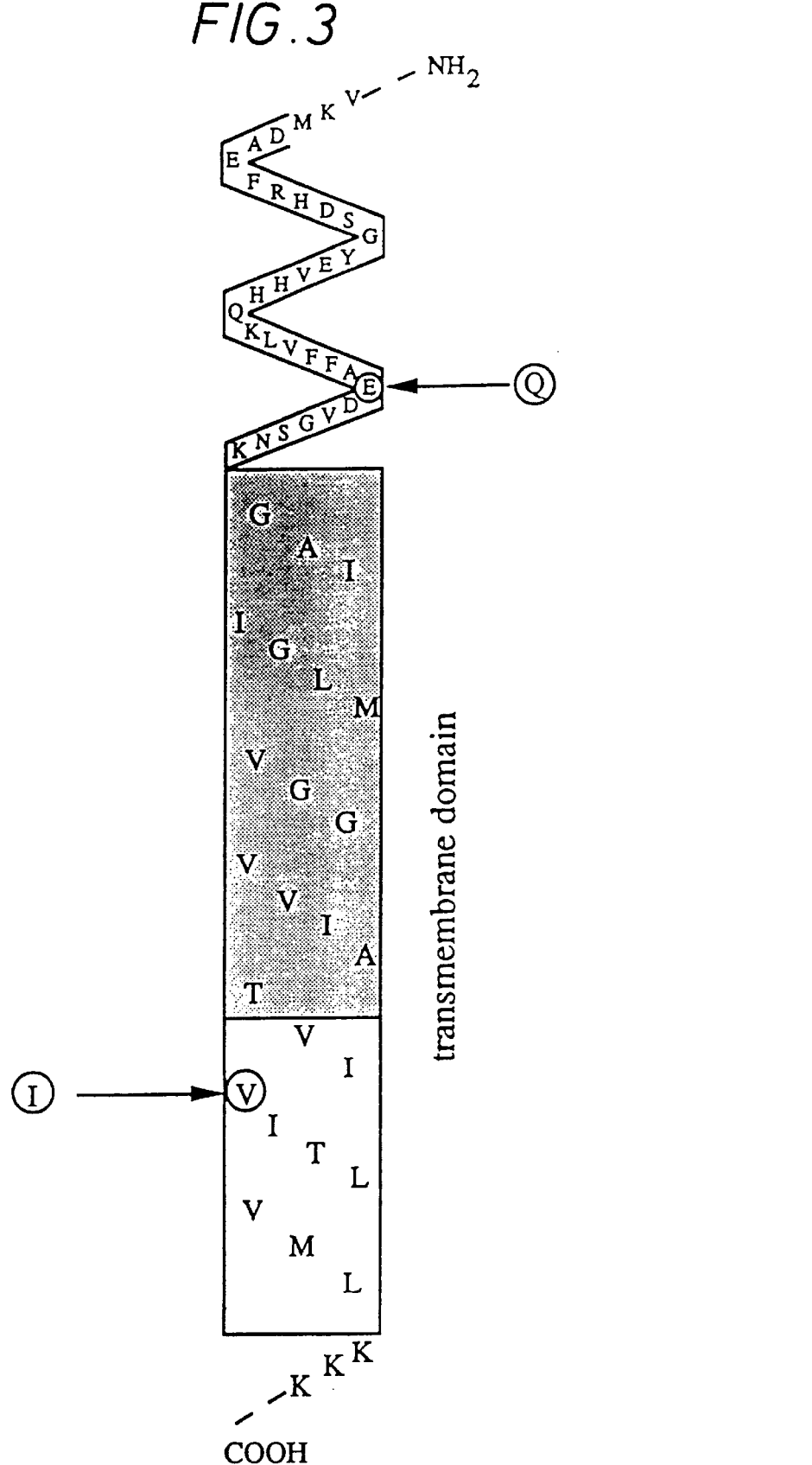
FIG. 3 shows part of the amino acid sequence encoded by exons 16 and 17 of the APP gene showing the mutation valine to isoleucine (V to I) within the transmembrane domain and the mutation causing HCHWA-D (E to Q) in the extracellular domain. The shaded region of the transmembrane domain and the boxed amino acids of the extracellular domain represent the sequence of the deposited β-amyloid peptide. Adapted from Kang et al. (1987) *Nature* 325:733.

Sequencing of exon 17 revealed a C to T transition at base pair 2149, causing a valine to isoleucine change at amino acid 717 (FIG. 2 and FIG. 3).

Figure 4:
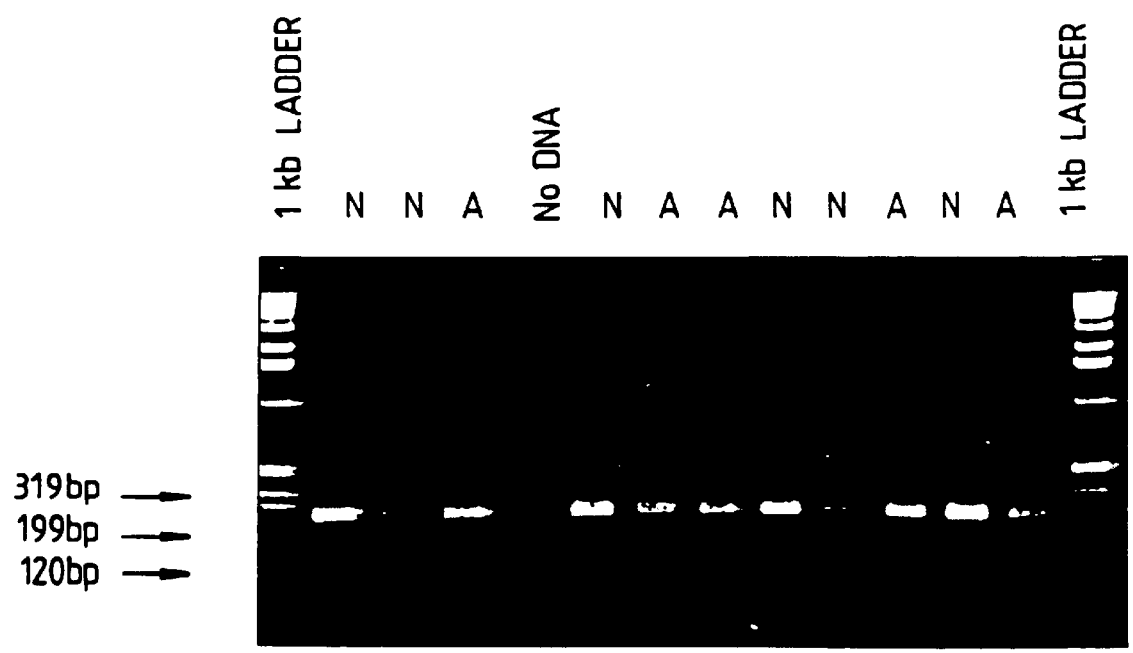
FIG. 4 shows BClI digests of the exon 17 PCR product from unaffected and affected individuals in an early onset AD family showing co-segregation of the restriction site and the disease.

This C to T transition creates a BclI restriction site enabling detection within the PCR product (FIG. 4). BclI digests were carried out at 50° C. for 2–4 hours, as recommended by the manufacturer, then electrophoresed in 3% agarose.

Screening by PCR of 100 unrelated, normal individuals and 14 cases (9 families) of familial late onset disease failed to demonstrate this substitution. Screening of 11 (9 families) cases of early onset familial disease revealed the BclI restriction site in two affected individuals from an unrelated family. The genetic data show that the disease loci are linked to the missense mutation. Also, failure to detect this polymorphism in 200 normal chromosomes supports the contention that it is a pathogenic mutation.

The valine to isoleucine substitution occurs within the transmembrane domain two residues from the C-terminus of the β-amyloid peptide. Computer analysis predicts that the substitution makes the transmembrane more hydrophobic and might thus anchor the protein more firmly within the membrane. The position of the substitution, two residues from the C-terminus of the β-amyloid peptide may be of significance to the origin of the deposited peptide. This finding Links Alzheimer's disease to HCHWA-D, a disease in which amyloid deposition is due to a mutation closer to the N-terminus but within the β-amyloid peptide (Levy et al. loc. cit.).

Example 2

Preparation of a cell line containing a defective β-amyloid (APP) gene 10 ml of fresh blood are collected from each individual suffering from familial Alzheimer's disease. Lymphocytes are purified from the blood on a Percoll gradient and mixed with Epstein-Barr virus (EBV). The cells are then plated out in medium supplemented with 10% foetal calf serum, antibiotics, glutamine and Cyclosporin A to kill the T lymphocytes. B lymphocytes which are infected by EBV become immortalized and establish a permanent cell line derived from the B cells of the patient.

A lymphoblastoid cell line, AC21, has been deposited with the European Collection of Animal Cell Cultures, Porton Down.

Example 3

Detection of a Val→Gly mutation in the β-amyloid (APP) gene

Figure 5:
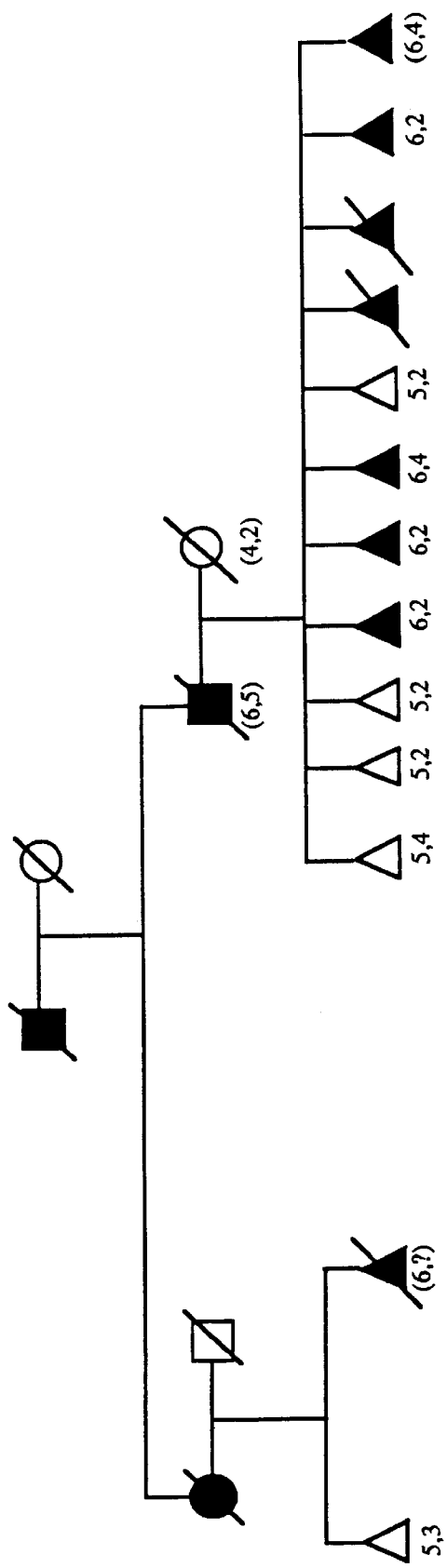
FIG. 5 shows the pedigree of family F19, together with D21S210 data.
Figure 6:
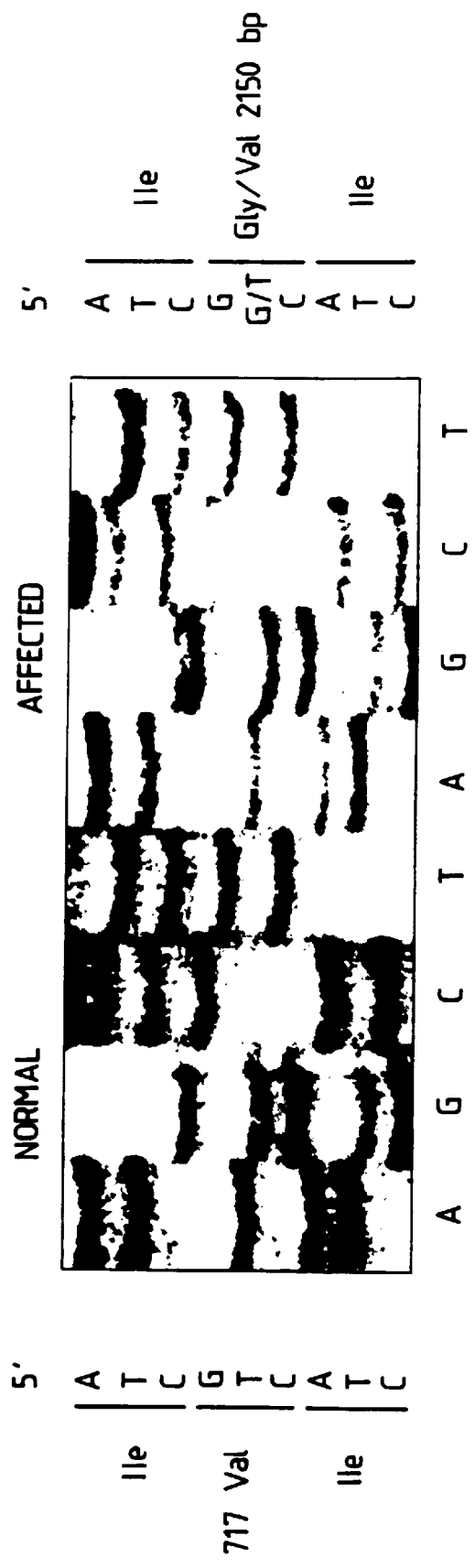
FIG. 6 shows APP exon 17 sequences in an affected and unaffected memberof F19. In the affected member there is a G→T transition at position 2150.

A pedigree, designated F19 and shown in FIG. 5, which has autopsy-confirmed AD with an onset age of 59±4 years was identified by observing that an allele of the highly polymorphic dinucleotide repeat marker GT12 (D21S210), which is located close to the APP gene, co-segregated with the disease. Linkage analysis gave a peak lod score between the marker and the disease of 3.02 at a recombination fraction of zero, as the following table shows:

| Theta | 0 | 0.01 | 0.05 | 0.1 | 0.2 | 0.3 | 0.4 |
|---|---|---|---|---|---|---|---|
| Lod | 3.02 | 2.97 | 2.75 | 2.47 | 1.86 | 1.22 | 0.6 |

Lod scores were calculated with seven liability classes modelling age-dependent penetrances from 0.01 to 0.95 with a phenocopy rate of 0.001 and a gene frequency of 0.001 using MLINK from the LINKAGE package (Lathrop et al. (1984) *Proc. Natl. Acad. Sci. USA* 81:3443).

APP exon 17 sequences in an affected and an unaffected member of F19 were determined. In the affected member, there was a G→T transition at position 2150, as can be seen from FIG. 6.

The amplification of exon 17 was performed as described in Example 1 above and Chartier-Harlin et al. (1991) *Neurosci. Letts.* 129:134, with the following modifications: (a) the amplification primer sequences were:

ATA-ACC-TCA-TCC-AAA-TGT-CCC-C [SEQ ID NO:28] and

GTA-ACC-CAA-GCA-TCA-TGG-AAG-C [SEQ ID NO:29]; and (b) the PCR conditions were 94° C./10 minutes then 35 cycles of 60° C./1 minute, 72° C./1 minute, 94° C./1 minute, followed by 72° C./5 minutes.

50 pmol of the second primer were used to generate single stranded product, which was then purified (Chartier-Harlin et al. loc. cit.). The purified product was sequenced with the SEQUENASE kit (2.0) (Trade mark; USB) using a primer of sequence:

AAA-TGA-AAT-TCT-TCT-AAT-TGC-G [SEQ ID NO:30].

The presence of the T→C transition creates gel artefacts which were resolved by the inclusion of inosine (SEQUENASE kit) in the sequencing reaction.

Direct sequencing of exons 7 and 16 from affected individuals from F19 (Chartier-Harlin et al. loc. cit.) shows that these were of normal sequence and SSCA (Orita et al. loc. cit.) and Orita et al.) failed to identify changes in exons 2, 3, 7, 9, 12, 13 or 15. SSCA of exon 17 detects both APP693 (Levy, et al. loc. cit. and Hardy et al. (1991) *Lancet* 337:1342–1343) and APP717 Val→Ile under standard screening conditions and, when modified APP717 Val→Gly.

Example 4

Production of Transgenic Animals with Mutant APP Allele

Generation of the constructs:

The vector plink was constructed by cloning polylinker between the PvuII and EcoRI sites of pBR322 such that the HindIII end of the polylinker was adjacent to the PvuII site. The ligation destroyed both the EcoR1 and PvuII sites associated with the pBR322 segments. The 700bp HpaI to EcoR1 fragment of pSV2neo (Southern and Berg (1982) *J. Mol. Appl. Genet.* 1:327) that contains the SV40 polyadenylation signal was cloned into the HpaI to EcoR1 sites of plink to generate pNotSV. The 200 bp XhoI to PstI fragment of pL2 containing the SV40 16S/1gS splice site (Okayama and Berg (1983) *Mol. Cell Biol.* 3:280) was isolated, blunted with Klenow, then cloned into the HpaI site of pNotSV to generate pSplice. The 2.3kb Nru1 to SpeI fragment of pAPP695 containing the coding region of the cDNA for APP (Tanzi et al. (1987) *Science* 235:880) was cloned into the NruI to SpeI site of pSplice to generate pd695. The same strategy was used to generate pd751 using the cDNA for APP751 (Tanzi et al. (1988) *Nature* 331:528). A variety of promoters have been inserted into the pd695 and pd751 vectors by using the unique NruI or the HindIII and NruI sites.

Generation of pshAPP695 & pshAPP751:

The construct pAmyproBam was generated by cloning the 1.5kb BamHI fragment of the APP cDNA into the BamHI site of puc19 xHamy. The 700 bp HindIII to Asp718 fragment of the pAmyproBam (similar to the 700 bp BamHI to Asp718 fragment described in Salbaum et al. (1988) *EMBO* 7:2807) was cloned into the HindIII to Asp718 sites of pd695 and pd751 to yield pshAPP695 and pshAPP751.

pAPP695 and pAPP751:

The pAPP695 and pAPP751 vectors were generated by a three-way ligation of the 3.0 kb EcoRI to XhoI fragment of pAmyProBam, the 1.5 kb XhoI to SpeI fragment of APP751cDNA, and the SpeI to EcoRI site of pd751.

Generation of pNSE751(+47):

The pNSE751 (+47) was constructed using a three-way ligation of the HindIII to KpnI fragment of pNSE6 (Forss-Petter et al. (1990) *Neuron* 5:187). The KpnI to BstY1 fragment of pNSE6 and a partial BamH1 (−47nt relative to the ATG) to HindIII fragment of pAPP751. This resulted in the generation of a KpnI fragment that was cloned into the KpnI sites of pNSE751(+47). The BstY1/Bam fusion results in the loss of both sites.

Generation of pNSE751:

This vector was generated using a four primer two-step PCR protocol (Higuchi et al. (1988) *Nucl. Acids Res.* 16:7351) that resulted in a direct fusion of the NSE initiation codon to the APP coding region. Oligonucleotides C2, 1072, 1073, and A2 (see Nucleotide Sequences, infra.) were used to generate a PCR product. The KpnI fragment was generated by digestion with the restriction enzyme. The KpnI fragment was used to replace a similar fragment in pNSE751 (+47).

Generation of pNSE751-Hardy and pNSE751-Dutch:

The Hardy (APP642 Val→Ile of APP695) and Dutch (APP618 Gln→Glu of APP695) mutations were introduced using a four primer two-PCR protocol. Both sets of reactions used the same "outside primers" with the "inside primers" containing the appropriate mutations. This resulted in the generation of BglII to SpeI fragment after digestion, that contained either the Dutch or the Hardy mutation. The BglII to SpeI fragment of pNSE751 was replaced by the mutated fragment to generate the appropriate vector. The presence of the mutation was conformed by sequence analysis of the vectors.

Generafion of pNSE75 1-Hardy and pNSE75 1-Dutch:

The Hardy VI (APP642 V to I), Hardy VG (APP642 V to G), and Dutch (APP618 E to Q) mutations were introduced using the four primer two-step PCR protocol (Higuchi et al. (1988)). The Hardy VI mutant was generated using primers 117/738, 922, 923, and 785; Hardy VG mutant was generated using primers 117/738, 1105, 1106, and 785; Dutch mutant was generated using primers 117/738, 1010, 1011, and 785. In all these mutations the 700 bp BglII to SpeI fragment was isolated by digestion of the PCR product with the restriction enzymes, then cloned into the same sites of pNSE751. The mutations were confirmed by sequence analysis.

Generation of pNFH751:

The human NFH gene (Lees et al. (1988) *EMBO* 7(7): 1947) was isolated from a genomic library using a rat NFH cDNA as a probe (Lieberburg et al. (1989) *Proc. Natl. Acids. Res. USA* 86:2463). An SstI fragment was subcloned into the pSK vector. A pair of PCR primers was generated to place a NruI site at the 3' end of the 150 bp amplified fragment immediately upstream of the initiation codon of the NFH gene. The 5' end contains a KpnI site 150nt upstream of the initiation codon. The final construction of pNFH751 was generated by a three-way ligation of the 5.5b HindIII to KpnI fragment of pNFH8.8, the KpnI to NruI PCR generated fragment, and the HindIII to NruI fragment of pd751. The sequence surrounding the PCR generated fusion at the initiation codon was confirmed by sequence analysis. The Dutch and Hardy variants of pNFH751 were generated by substitution of the 600 bp BgIII to SpeI fragment from a sequence confirmed mutated vector for the same fragment of pNFH751. The presence of the mutation was confirmed by hybridization with the mutated oligomer or by sequence analysis.

Generation of pThy751:

The pThy751 vector was generated by a three-way ligation. The HindIII to BamHI fragment of pThy8.2 which was isolated from a human genomic library (Chang et al. (1985) *Proc. Natl. Acad. Sci. USA* 82:3819), the synthetic fragment ThyAPP, and the HindIII to NruI fragment of pd751.

ThyAPP:

CAGACTGAGATCCCAGAACCCTAGGTCTGACTC-TAGGGTCTTGG[SEQ ID NO:31]

Generation of pThyC100:

This pThyC100 construct was generated by a three-way ligation. The 3.6kb HindIII to BamH1 fragment of pThy8.2, the synthetic fragment ThyAPP2, and the HindIII to BglII fragment of pd751 or pNSE751 Dutch or pNSE751 Hardy were ligated to yield pThyC100.

ThyAPP2:

CAGACTGAGATCCCAGAACCGATCCTAG-GTCTGACTCTAGGGTCTrGG [SEQ ID NO:32]

The region around the initiation codon was confirmed by sequence analysis.

Preparation of DNA for injection:

The transgene for injection was isolated from the corresponding vector of interest for digestion with NotI and gel electrophoresis. The transgene was purified by using the Gene Clean kit (Bio101), then further purified on an Elutip or HPLC purified on a Nucleogen 4000 column.

Microinjection:

The transgene was injected at 2–20 mcg/ml into the most convenient pronucleus (usually the male pronucleus) of FVB or B6D2F2 one-cell embryos (Manipulating the Mouse Embryo, B. Hogan, F. Constantini, E. Lacy, Cold Spring Harbor, 1986). The injected embryos were cultured overnight. Embryos that split to the two-cell stage were implanted into pseudo-pregnant female CD1 mice. The mice were weaned at approximately 21 days. Samples of DNA obtained from tail biopsy were analyzed by Southern blot using a transgene specific probe (usually the SV40 3's splice and polyadenylation signal sequences). Transgenic mice harboring at least one copy of the transgene were identified.

Use of Transgenic Mice: A mouse that expresses the hAPP gene or its variants can be used to test the pathogenesis of amyloid deposition and therapeutic intervention designed to modulate amyloid deposition.

Biochemical analysis of the transgenic mice reveals possible intermediates in the catabolism of APP that are likely precursors to beta-amyloid. This analysis can be carried out in the animal or in primary tissue culture of the expressing cells.

The animal can be used to test potential therapeutic agents. The test group of mice is treated with the test compound administered in an appropriate fashion for a set period. At the conclusion of the test period, the animals are assessed behaviourally, biochemically, and histologically for any possible effects of the test compound. The exact protocol depends on the anticipated mechanism of action of the test compound. Compounds that may have utility in treating AD can be identified using this approach.

What is claimed is:

1. A transgenic mouse whose genome comprises a nucleic acid construct comprising a heterologous DNA sequence encoding a position 717 mutant of an amyloid precursor polypeptide 770 (APP770) (SEQ ID NO:3), or of another isoform of APP, operably linked to a promoter, wherein expression of the nucleic acid construct in brain cells of the mouse results in the production of detectable levels of the amyloid precursor polypeptide in the brain of the mouse.

2. The transgenic mouse of claim 1, wherein the heterologous DNA sequence encodes a human APP polypeptide.

3. A transgenic mouse whose genome comprises nucleic acid construct comprising a heterologous DNA sequence encoding an APP comprising Ile-Ala-Thr-Val-Ile-X-Ile-Thr-Leu (SEQ ID No:6), wherein X is any of the twenty naturally occurring amino acid other than valine operably linked to a promoter, wherein expression of the nucleic acid construct in brain cells of the mouse results in the production of detectable levels of the amyloid precursor polypeptide in the brain of the mouse.

4. A transgenic mouse whose genome comprises nucleic acid construct comprising heterologous DNA sequence encoding a familial Alzheimer's Disease (FAD) amyloid precursor polypeptide operably linked to a promoter, wherein expression of the nucleic acid construct in brain cells of the mouse results in the production of detectable levels of the amyloid precursor polypeptide in the brain of the mouse.

5. A method of screening for an agent capable of treating Alzheimer's Disease comprising:

administering an agent to a transgenic mouse whose genome comprises a nucleic acid construct comprising a heterologous DNA sequence encoding a position 717 mutant of an amyloid precursor polypeptide 770 (APP770) (SEQ ID NO:3), or of another isoform of APP, operably linked to a promoter, wherein expression of the nucleic acid construct in brain cells of the mouse results in the production of detectable levels of the amyloid precursor polypeptide in the brain of the mouse; and monitoring the agent's effect on production of detectable levels of the amyloid precursor polypeptide in the brain of the mouse.

6. A method of screening for an agent capable of treating Alzheimer's Disease comprising:

administering an agent to a transgenic mouse whose genome comprises a nucleic acid construct comprising a heterologous DNA sequence encoding a familial Alzheimer's Disease (FAD) variant of amyloid precursor polypeptide 770 (APP770) (SEQ ID NO:3), or another FAD isoform of APP, operably linked to a promoter, wherein expression of the nucleic acid construct in brain cells of the mouse results in the production of detectable levels of the amyloid precursor polypeptide in the brain of the mouse; and monitoring the agent's effect on production of detectable levels of the amyloid precursor polypeptide in the brain of the mouse.

* * * * *

SEQUENCE LISTING (1) GENERAL INFORMATION:

(iii) NUMBER OF SEQUENCES: 44

(2) INFORMATION FOR SEQ ID NO: 1:

(i) SEQUENCE CHARACTERISTICS:
      (A) LENGTH: 695 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
        260                 265                 270

Ala Thr Thr Thr Thr Thr Thr Thr Glu Ser Val Glu Glu Val Val Arg
    275                 280                 285
```

```
Val Pro Thr Thr Ala Ala Ser Thr Pro Asp Ala Val Asp Lys Tyr Leu
    290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
        355                 360                 365
Gln Glu Ala Ala Asn Glu Arg Gln Gln Leu Val Glu Thr His Met Ala
    370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
        435                 440                 445
Ala Gln Ile Arg Ser Gln Val Met Thr His Leu Arg Val Ile Tyr Glu
    450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
Tyr Gly Asn Asp Ala Leu Met Pro Ser Leu Thr Glu Thr Lys Thr Thr
        515                 520                 525
Val Glu Leu Leu Pro Val Asn Gly Glu Phe Ser Leu Asp Asp Leu Gln
    530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Met Asp Ala Glu Phe Arg His Asp Ser Gly Tyr Glu Val
        595                 600                 605
His His Gln Lys Leu Val Phe Phe Ala Glu Asp Val Gly Ser Asn Lys
    610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
        675                 680                 685
Phe Phe Glu Gln Met Gln Asn
    690                 695
```

(2) INFORMATION FOR SEQ ID NO: 2:

(i) SEQUENCE CHARACTERISTICS:
        (A) LENGTH: 751 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met Leu Pro Gly Leu Ala Leu Leu Leu Ala Ala Trp Thr Ala Arg
 1               5                  10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
            195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
275                 280                 285

Glu Val Cys Ser Glu Gln Ala Glu Thr Gly Pro Cys Arg Ala Met Ile
            290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Ile Pro Thr Thr Ala Ala Ser Thr
            340                 345                 350
```

```
Pro Asp Ala Val Asp Lys Tyr Leu Glu Thr Pro Gly Asp Glu Asn Glu
        355                 360                 365

His Ala His Phe Gln Lys Ala Lys Glu Arg Leu Glu Ala Lys His Arg
        370                 375                 380

Glu Arg Met Ser Gln Val Met Arg Glu Trp Glu Ala Glu Arg Gln
385                 390                 395                 400

Ala Lys Asn Leu Pro Lys Ala Asp Lys Lys Ala Val Ile Gln His Phe
                405                 410                 415

Gln Glu Lys Val Glu Ser Leu Glu Gln Glu Ala Ala Asn Glu Arg Gln
            420                 425                 430

Gln Leu Val Glu Thr His Met Ala Arg Val Glu Ala Met Leu Asn Asp
        435                 440                 445

Arg Arg Arg Leu Ala Leu Glu Asn Tyr Ile Thr Ala Leu Gln Ala Val
    450                 455                 460

Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
                485                 490                 495

Arg Met Val Asp Pro Lys Lys Ala Ala Gln Ile Arg Ser Gln Val Met
            500                 505                 510

Thr His Leu Arg Val Ile Tyr Glu Arg Met Asn Gln Ser Leu Ser Leu
        515                 520                 525

Leu Tyr Asn Val Pro Ala Val Ala Glu Glu Ile Gln Asp Glu Val Asp
        530                 535                 540

Glu Leu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
                565                 570                 575

Ser Leu Thr Glu Thr Lys Thr Thr Val Glu Leu Leu Pro Val Asn Gly
            580                 585                 590

Glu Phe Ser Leu Asp Asp Leu Gln Pro Trp His Ser Phe Gly Ala Asp
        595                 600                 605

Ser Val Pro Ala Asn Thr Glu Asn Glu Val Glu Pro Val Asp Ala Arg
610                 615                 620

Pro Ala Ala Asp Arg Gly Leu Thr Thr Arg Pro Gly Ser Gly Leu Thr
625                 630                 635                 640

Asn Ile Lys Thr Glu Glu Ile Ser Glu Val Lys Met Asp Ala Glu Phe
                645                 650                 655

Arg His Asp Ser Gly Tyr Glu Val His His Gln Lys Leu Val Phe Phe
            660                 665                 670

Ala Glu Asp Val Gly Ser Asn Lys Gly Ala Ile Ile Gly Leu Met Val
        675                 680                 685

Gly Gly Val Val Ile Ala Thr Val Ile Val Ile Thr Leu Val Met Leu
        690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn
            740                 745                 750
```

(2) INFORMATION FOR SEQ ID NO: 3:

(i) SEQUENCE CHARACTERISTICS:

(A) LENGTH: 770 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 3:

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp

```
                    370                 375                 380
Glu Asn Glu His Ala His Phe Gln Lys Ala Lys Glu Arg Leu Glu Ala
385                 390                 395                 400
Lys His Arg Glu Arg Met Ser Gln Val Met Arg Glu Trp Glu Glu Ala
                    405                 410                 415
Glu Arg Gln Ala Lys Asn Leu Pro Lys Ala Asp Lys Lys Ala Val Ile
                    420                 425                 430
Gln His Phe Gln Glu Lys Val Glu Ser Leu Glu Gln Glu Ala Ala Asn
                    435                 440                 445
Glu Arg Gln Gln Leu Val Glu Thr His Met Ala Arg Val Glu Ala Met
450                 455                 460
Leu Asn Asp Arg Arg Arg Leu Ala Leu Glu Asn Tyr Ile Thr Ala Leu
465                 470                 475                 480
Gln Ala Val Pro Pro Arg Pro Arg His Val Phe Asn Met Leu Lys Lys
                    485                 490                 495
Tyr Val Arg Ala Glu Gln Lys Asp Arg Gln His Thr Leu Lys His Phe
                    500                 505                 510
Glu His Val Arg Met Val Asp Pro Lys Lys Ala Ala Gln Ile Arg Ser
                    515                 520                 525
Gln Val Met Thr His Leu Arg Val Ile Tyr Glu Arg Met Asn Gln Ser
530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                    565                 570                 575
Leu Ala Asn Met Ile Ser Glu Pro Arg Ile Ser Tyr Gly Asn Asp Ala
                    580                 585                 590
Leu Met Pro Ser Leu Thr Glu Thr Lys Thr Thr Val Glu Leu Leu Pro
                    595                 600                 605
Val Asn Gly Glu Phe Ser Leu Asp Asp Leu Gln Pro Trp His Ser Phe
610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                    645                 650                 655
Gly Leu Thr Asn Ile Lys Thr Glu Glu Ile Ser Glu Val Lys Met Asp
                    660                 665                 670
Ala Glu Phe Arg His Asp Ser Gly Tyr Glu Val His His Gln Lys Leu
                    675                 680                 685
Val Phe Phe Ala Glu Asp Val Gly Ser Asn Lys Gly Ala Ile Ile Gly
                    690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                    725                 730                 735
Glu Val Asp Ala Ala Val Thr Pro Glu Glu Arg His Leu Ser Lys Met
                    740                 745                 750
Gln Gln Asn Gly Tyr Glu Asn Pro Thr Tyr Lys Phe Phe Glu Gln Met
                    755                 760                 765
Gln Asn
    770

(2) INFORMATION FOR SEQ ID NO: 4:
```

(i) SEQUENCE CHARACTERISTICS:
    (A) LENGTH: 2088 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 4:

```
ATGCTGCCCG GTTTGGCACT GCTCCTGCTG GCCGCCTGGA CGGCTCGGGC GCTGGAGGTA      60
CCCACTGATG GTAATGCTGG CCTGCTGGCT GAACCCCAGA TTGCCATGTT CTGTGGCAGA     120
CTGAACATGC ACATGAATGT CCAGAATGGG AAGTGGGATT CAGATCCATC AGGGACCAAA     180
ACCTGCATTG ATACCAAGGA AGGCATCCTG CAGTATTGCC AAGAAGTCTA CCCTGAACTG     240
CAGATCACCA ATGTGGTAGA AGCCAACCAA CCAGTGACCA TCCAGAACTG GTGCAAGCGG     300
GGCCGCAAGC AGTGCAAGAC CCATCCCCAC TTTGTGATTC CCTACCGCTG CTTAGTTGGT     360
GAGTTTGTAA GTGATGCCCT TCTCGTTCCT GACAAGTGCA AATTCTTACA CCAGGAGAGG     420
ATGGATGTTT GCGAAACTCA TCTTCACTGG CACACCGTCG CCAAAGAGAC ATGCAGTGAG     480
AAGAGTACCA ACTTGCATGA CTACGGCATG TTGCTGCCCT GCGGAATTGA CAAGTTCCGA     540
GGGGTAGAGT TTGTGTGTTG CCCACTGGCT GAAGAAAGTG ACAATGTGGA TTCTGCTGAG     600
GCGGAGGAGG ATGACTCGGA TGTCTGGTGG GGCGGAGCAG ACACAGACTA TGCAGATGGG     660
AGTGAAGACA AAGTAGTAGA AGTAGCAGAG GAGGAAGAAG TGGCTGAGGT GGAAGAAGAA     720
GAAGCCGATG ATGACGAGGA CGATGAGGAT GGTGATGAGG TAGAGGAAGA GGCTGAGGAA     780
CCCTACGAAG AAGCCACAGA GAGAACCACC AGCATTGCCA CCACCACCAC CACCACCACA     840
GAGTCTGTGG AAGAGGTGGT TCGAGTTCCT ACAACAGCAG CCAGTACCCC TGATGCCGTT     900
GACAAGTATC TCGAGACACC TGGGGATGAG AATGAACATG CCCATTTCCA GAAAGCCAAA     960
GAGAGGCTTG AGGCCAAGCA CCGAGAGAGA ATGTCCCAGG TCATGAGAGA ATGGGAAGAG    1020
GCAGAACGTC AAGCAAAGAA CTTGCCTAAA GCTGATAAGA AGGCAGTTAT CCAGCATTTC    1080
CAGGAGAAAG TGGAATCTTT GGAACAGGAA GCAGCCAACG AGAGACAGCA GCTGGTGGAG    1140
ACACACATGG CCAGAGTGGA AGCCATGCTC AATGACCGCC GCCGCCTGGC CCTGGAGAAC    1200
TACATCACCG CTCTGCAGGC TGTTCCTCCT CGGCCTCGTC ACGTGTTCAA TATGCTAAAG    1260
AAGTATGTCC GCGCAGAACA GAAGGACAGA CAGCACACCC TAAAGCATTT CGAGCATGTG    1320
CGCATGGTGG ATCCCAAGAA AGCCGCTCAG ATCCGGTCCC AGGTTATGAC ACACCTCCGT    1380
GTGATTTATG AGCGCATGAA TCAGTCTCTC TCCCTGCTCT ACAACGTGCC TGCAGTGGCC    1440
GAGGAGATTC AGGATGAAGT TGATGAGCTG CTTCAGAAAG AGCAAAACTA TTCAGATGAC    1500
GTCTTGGCCA ACATGATTAG TGAACCAAGG ATCAGTTACG GAAACGATGC TCTCATGCCA    1560
TCTTTGACCG AAACGAAAAC CACCGTGGAG CTCCTTCCCG TGAATGGAGA GTTCAGCCTG    1620
GACGATCTCC AGCCGTGGCA TTCTTTTGGG GCTGACTCTG TGCCAGCCAA CACAGAAAAC    1680
GAAGTTGAGC CTGTTGATGC CCGCCCTGCT GCCGACCGAG GACTGACCAC TCGACCAGGT    1740
TCTGGGTTGA CAAATATCAA GACGGAGGAG ATCTCTGAAG TGAAGATGGA TGCAGAATTC    1800
CGACATGACT CAGGATATGA AGTTCATCAT CAAAAATTGG TGTTCTTTGC AGAAGATGTG    1860
GGTTCAAACA AAGGTGCAAT CATTGGACTC ATGGTGGGCG GTGTTGTCAT AGCGACAGTG    1920
ATCGTCATCA CCTTGGTGAT GCTGAAGAAG AAACAGTACA CATCCATTCA TCATGGTGTG    1980
GTGGAGGTTG ACGCCGCTGT CACCCCAGAG GAGCGCCACC TGTCCAAGAT GCAGCAGAAC    2040
```

```
GGCTACGAAA ATCCAACCTA CAAGTTCTTT GAGCAGATGC AGAACTAG                2088
```

(2) INFORMATION FOR SEQ ID NO: 5:

(i) SEQUENCE CHARACTERISTICS:
        (A) LENGTH: 2265 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
ATGCTGCCCG GTTTGGCACT GCTCCTGCTG GCCGCCTGGA CGGCTCGGGC GCTGGAGGTA    60

CCCACTGATG GTAATGCTGG CCTGCTGGCT GAACCCCAGA TTGCCATGTT CTGTGGCAGA   120

CTGAACATGC ACATGAATGT CCAGAATGGG AAGTGGGATT CAGATCCATC AGGGACCAAA   180

ACCTGCATTG ATACCAAGGA AGGCATCCTG CAGTATTGCC AAGAAGTCTA CCCTGAACTG   240

CAGATCACCA ATGTGGTAGA AGCCAACCAA CCAGTGACCA TCCAGAACTG GTGCAAGCGG   300

GGCCGCAAGC AGTGCAAGAC CCATCCCCAC TTTGTGATTC CCTACCGCTG CTTAGTTGGT   360

GAGTTTGTAA GTGATGCCCT TCTCGTTCCT GACAAGTGCA AATTCTTACA CCAGGAGAGG   420

ATGGATGTTT GCGAAACTCA TCTTCACTGG CACACCGTCG CCAAAGAGAC ATGCAGTGAG   480

AAGAGTACCA ACTTGCATGA CTACGGCATG TTGCTGCCCT GCGGAATTGA CAAGTTCCGA   540

GGGGTAGAGT TTGTGTGTTG CCCACTGGCT GAAGAAAGTG ACAATGTGGA TTCTGCTGAT   600

GCGGAGGAGG ATGACTCGGA TGTCTGGTGG GGCGGAGCAG ACACAGACTA TGCAGATGGG   660

AGTGAAGACA AAGTAGTAGA AGTAGCAGAG GAGGAAGAAG TGGCTGAGGT GGAAGAAGAA   720

GAAGCCGATG ATGACGAGGA CGATGAGGAT GGTGATGAGG TAGAGGAAGA GGCTGAGGAA   780

CCCTACGAAG AAGCCACAGA GAGAACCACC AGCATTGCCA CCACCACCAC CACCACCACA   840

GAGTCTGTGG AAGAGGTGGT TCGAGAGGTG TGCTCTGAAC AAGCCGAGAC GGGGCCGTGC   900

CGAGCAATGA TCTCCCGCTG GTACTTTGAT GTGACTGAAG GGAAGTGTGC CCCATTCTTT   960

TACGGCGGAT GTGGCGGCAA CCGGAACAAC CGGAACAACT TTGACACAGA AGAGTACTGC  1020

ATGGCCGTGT GTGGCAGCGC CATTCCTACA ACAGCAGCCA GTACCCCTGA TGCCGTTGAC  1080

AAGTATCTCG AGACACCTGG GGATGAGAAT GAACATGCCC ATTTCCAGAA AGCCAAAGAG  1140

AGGCTTGAGG CCAAGCACCG AGAGAGAATG TCCCAGGTCA TGAGAGAATG GGAAGAGGCA  1200

GAACGTCAAG CAAAGAACTT GCCTAAAGCT GATAAGAAGG CAGTTATCCA GCATTTCCAG  1260

GAGAAAGTGG AATCTTTGGA ACAGGAAGCA GCCAACGAGA GACAGCAGCT GGTGGAGACA  1320

CACATGGCCA GAGTGGAAGC CATGCTCAAT GACCGCCGCC GCCTGGCCCT GGAGAACTAC  1380

ATCACCGCTC TGCAGGCTGT TCCTCCTCGG CCTCGTCACG TGTTCAATAT GCTAAAGAAG  1440

TATGTCCGCG CAGAACAGAA GGACAGACAG CACACCCTAA AGCATTTCGA GCATGTGCGC  1500

ATGGTGGATC CCAAGAAAGC CGCTCAGATC CGGTCCCAGG TTATGACACA CCTCCGTGTG  1560

ATTTATGAGC GCATGAATCA GTCTCTCTCC CTGCTCTACA ACGTGCCTGC AGTGGCCGAG  1620

GAGATTCAGG ATGAAGTTGA TGAGCTGCTT CAGAAAGAGC AAAACTATTC AGATGACGTC  1680

TTGGCCAACA TGATTAGTGA ACCAAGGATC AGTTACGGAA ACGATGCTCT CATGCCATCT  1740

TTGACCGAAA CGAAAACCAC CGTGGAGCTC CTTCCCGTGA ATGGAGAGTT CAGCCTGGAC  1800

GATCTCCAGC CGTGGCATTC TTTTGGGGCT GACTCTGTGC CAGCCAACAC AGAAAACGAA  1860

GTTGAGCCTG TTGATGCCCG CCCTGCTGCC GACCGAGGAC TGACCACTCG ACCAGGTTTC  1920
```

-continued

```
GGGTTGACAA ATATCAAGAC GGAGGAGATC TCTGAAGTGA AGATGGATGC AGAATTCCGA    1980

CATGACTCAG GATATGAAGT TCATCATCAA AAATTGGTGT TCTTTGCAGA AGATGTGGGT    2040

TCAAACAAAG GTGCAATCAT TGGACTCATG GTGGGCGGTG TTGTCATAGC GACAGTGATC    2100

GTCATCACCT TGGTGATGCT GAAGAAGAAA CAGTACACAT CCATTCATCA TGGTGTGGTG    2160

GAGGTTGACG CCGCTGTCAC CCCAGAGGAG CGCCACCTGT CCAAGATGCA GCAGAACGGC    2220

TACGAAAATC CAACCTACAA GTTCTTTGAG CAGATGCAGA ACTAG                    2265
```

(2) INFORMATION FOR SEQ ID NO: 6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Ile Ala Thr Val Ile Xaa Ile Thr Leu
1          5

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

Ile Ala Thr Val Ile Gly Ile Thr Leu
1          5

(2) INFORMATION FOR SEQ ID NO: 8:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Ile Ala Thr Val Ile Met Ile Thr Leu
1          5

(2) INFORMATION FOR SEQ ID NO: 9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

Ile Ala Thr Val Ile Ala Ile Thr Leu
1          5

(2) INFORMATION FOR SEQ ID NO: 10:

```
        (i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 10:

Ile Ala Thr Val Ile Ser Ile Thr Leu
1               5

(2) INFORMATION FOR SEQ ID NO: 11:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 11:

Ile Ala Thr Val Ile Ile Ile Thr Leu
1               5

(2) INFORMATION FOR SEQ ID NO: 12:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 12:

Ile Ala Thr Val Ile Leu Ile Thr Leu
1               5

(2) INFORMATION FOR SEQ ID NO: 13:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 13:

Ile Ala Thr Val Ile Thr Ile Thr Leu
1               5

(2) INFORMATION FOR SEQ ID NO: 14:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 14:

Ile Ala Thr Val Ile Pro Ile Thr Leu
1               5

(2) INFORMATION FOR SEQ ID NO: 15:
```

```
        (i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 15:

Ile Ala Thr Val Ile His Ile Thr Leu
1               5

(2) INFORMATION FOR SEQ ID NO: 16:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 16:

Ile Ala Thr Val Ile Cys Ile Thr Leu
1               5

(2) INFORMATION FOR SEQ ID NO: 17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 17:

Ile Ala Thr Val Ile Tyr Ile Thr Leu
1               5

(2) INFORMATION FOR SEQ ID NO: 18:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 18:

Ile Ala Thr Val Ile Phe Ile Thr Leu
1               5

(2) INFORMATION FOR SEQ ID NO: 19:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO: 19:

Ile Ala Thr Val Ile Glu Ile Thr Leu
1               5
```

(2) INFORMATION FOR SEQ ID NO: 20:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 20:

Ile Ala Thr Val Ile Trp Ile Thr Leu
1               5

(2) INFORMATION FOR SEQ ID NO: 21:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 21:

Ile Ala Thr Val Ile Arg Ile Thr Leu
1               5

(2) INFORMATION FOR SEQ ID NO: 22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 22:

Ile Ala Thr Val Ile Asp Ile Thr Leu
1               5

(2) INFORMATION FOR SEQ ID NO: 23:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 23:

Ile Ala Thr Val Ile Asn Ile Thr Leu
1               5

(2) INFORMATION FOR SEQ ID NO: 24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 24:

Ile Ala Thr Val Ile Lys Ile Thr Leu
1               5

(2) INFORMATION FOR SEQ ID NO: 25:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 25:

```
Ile Ala Thr Val Ile Gln Ile Thr Leu
1               5
```

(2) INFORMATION FOR SEQ ID NO: 26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (Primer)

(xi) SEQUENCE DESCRIPTION: SEQ ID NO: 26:

```
CCTCATCCAA ATGTCCCCGT CATT                                              24
```

(2) INFORMATION FOR SEQ ID NO: 27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (Primer)

(xi) SEQUENCE DESCRIPTION: SEQ ID NO: 27:

```
GCCTAATTCT CTCATAGTCT TAATTCCCAC                                        30
```

(2) INFORMATION FOR SEQ ID NO: 28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (Primer)

(xi) SEQUENCE DESCRIPTION: SEQ ID NO: 28:

```
ATAACCTCAT CCAAATGTCC CC                                                22
```

(2) INFORMATION FOR SEQ ID NO: 29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (Primer)

(xi) SEQUENCE DESCRIPTION: SEQ ID NO: 29:

```
GTAACCCAAG CATCATGGAA GC                                                22
```

(2) INFORMATION FOR SEQ ID NO: 30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (Primer)

(xi) SEQUENCE DESCRIPTION: SEQ ID NO: 30:

AAATGAAATT CTTCTAATTG CG                                                    22

(2) INFORMATION FOR SEQ ID NO: 31:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

CAGACTGAGA TCCCAGAACC CTAGGTCTGA CTCTAGGGTC TTGG                            44

(2) INFORMATION FOR SEQ ID NO: 32:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (Primer)

(xi) SEQUENCE DESCRIPTION: SEQ ID NO: 32:

CAGACTGAGA TCCCAGAACC GATCCTAGGT CTGACTCTAG GGTCTTGG                        48

(2) INFORMATION FOR SEQ ID NO: 33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

CGACCAGGTT GTGGGTTGAC AAATA                                                 25

(2) INFORMATION FOR SEQ ID NO: 34:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

AATCTATTCA TGCACTAGTT TGATACAGC                                             29

(2) INFORMATION FOR SEQ ID NO: 35:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 35:

ACAGTGATCA TCATCACCTT G                                            21

(2) INFORMATION FOR SEQ ID NO: 36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

CAAGGTGATG ATGATCACTG T                                            21

(2) INFORMATION FOR SEQ ID NO: 37:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

AGCGACAGTG ATCGGCATCA CCTTGGTG                                     28

(2) INFORMATION FOR SEQ ID NO: 38:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

CACCCAGGTG ATGCCGATCA CTGTCGCT                                     28

(2) INFORMATION FOR SEQ ID NO: 39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

ACCCACATCT TGTGCAAAGA ACAC                                         24

(2) INFORMATION FOR SEQ ID NO: 40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO: 40:

GTGTTCTTTG CACAAGATGT GGGT                                              24

(2) INFORMATION FOR SEQ ID NO: 41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

CCCAGCCATC ATGCTGCCCG GGTTGGC                                           27

(2) INFORMATION FOR SEQ ID NO: 42:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

GCCAACCCGG GCAGCATGAT GACTGGGATC TC                                     32

(2) INFORMATION FOR SEQ ID NO: 43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

ACCTGCCACT ATACTGGAAT A                                                 21

(2) INFORMATION FOR SEQ ID NO: 44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

TGTGCATGTT CAGTCTGCCA C                                                 21